US006322985B1

(12) United States Patent
Kashi et al.

(10) Patent No.: US 6,322,985 B1
(45) Date of Patent: *Nov. 27, 2001

(54) ABUNDANT, WELL DISTRIBUTED AND HYPERPOLYMORPHIC SIMPLE SEQUENCE REPEATS IN PROKARYOTE GENOMES AND USE OF SAME FOR PROKARYOTE CLASSIFICATION AND TYPING

(75) Inventors: Yechezkel Kashi, Haifa; Riva Gur-Arie, Binyamina; Cyril Cohen, Nebher; Yuval Eitan, Jerusalem, all of (IL); Leora Shelef, Bloomfield Vill., MI (US); Eric Hallerman, Blacksburg, VA (US)

(73) Assignee: Technion Research and Development Foundation Ltd., Haifa (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/472,035

(22) Filed: Dec. 27, 1999

(51) Int. Cl.⁷ .............................. C12Q 1/68; C12P 19/34; C07H 2/104
(52) U.S. Cl. ........................... 435/6; 435/91.2; 536/23.1; 536/24.3
(58) Field of Search ..................... 435/6, 91.2; 531/23.1, 531/24.3

(56) References Cited

PUBLICATIONS

Van Belkum et al, "Short–sequence DNA repeats in prokaryotic genomes", Microbiol. Mol. Biol. Rev. 62(2):275–293, Jun. 1998.*

Gingeras et al, "Simultaneous genotyping and species identification using hybridization pattern recognition analysis of generic mycobacterium DNA arrays", Genome Research 8:435–448, May 1998.*

Busse et al, "Classification and identification of bacteria: current approaches to an old problem.", Journal of Biotechnology 47:3–38, Jan. 1996.*

Widjojoatmodjo et al, "Molecular identification of bacteria by fluorescence based PCR single strand conformation polymorphism analysis of the 16S rRNA gene", Journal of Clinical Microbiology 33(10):2601–2606, Oct. 1995.*

* cited by examiner

*Primary Examiner*—Jeffrey Fredman

(57) ABSTRACT

A method is provided for classifying or typing a prokaryote to a class or a type. The method is effected by characterizing at least one polymorphic simple sequence repeat locus in a genome of the prokaryote and, based on a characterization of the polymorphic simple sequence repeat, classifying or typing the prokaryote to a class or a type. Compounds and articles of manufacture are provided for effecting the method.

17 Claims, 8 Drawing Sheets

```
                       1                                                     50
Ec K12, DH5α   ---GTTATGT CTTATCCCAC GGTATTTAAT ATGGTTCATT AGGATGTTTA 25*
Ec Bsr9b       -TTGTTATGT CTTATCCCAC GGTATTTAAT ATAGTTCATT TGGATGTTCA 26*
Ec Bsr9c       TTTGTTATGT CTTATCCCAC GGTATTTAAT ATAGTTCATT TGGATGTTCA 27*
Ec ETEC        -TCTATGTTC TTATCNCCAC GGTNTTTAAT ATGGTtCATT AGGATGTTTA 28*

Consensus   -----T-T-- -T---CCCAC GGTATTTAAT AT-GTTCATT -GGATGTT-A 29*

51                                                   100
Ec K12, DH5α   TTTCTTGATT TTGCATATGA GTATATTA.. CCCCCCCCTC AAAAAAATAA
Ec Bsr9b       TTTCTTTATT TTGCATATGA GTATATTA.. ....CCCCTT CAAAAAATAA
Ec Bsr9c       TTTCTTTATT TTGCATATGA GTATATTA.. ....CCCCTT CAAAAAATAA
Ec ETEC        TTTCTTGATT TTGCATATGA GTATATTACC CCCCCCCCTC AAAAAAATAA

Consensus   TTTCTT-ATT TTGCATATGA GTATATTA-- ----CCCCT- -AAAAAATAA 101                                                  150
Ec K12, DH5α   ATTAATTAAA ATGATGGCTT ATATAAAATA AAATTTAAAG CAAGGAATCT
Ec Bsr9b       ATTAATTAAA ACGATTGCTT ATATAAAACA AAATTTAAAG CAAGGAATCT
Ec Bsr9c       ATTAATTAAA ACGATTGCTT ATATAAAACA AAATTTAAAG CAAGGAATCT
Ec ETEC        ATTAATTAAA ATGATGGCTT ATATNAAATA NAATTTAAAG CAAGGANTCT Consensus   ATTAATTAAA A-GAT-GCTT ATATAAAA-A AAATTTAAAG CAAGGAATCT 151                                                  200
Ec K12, DH5α   CAATGGATGT TAAACAAAAT GAGATTTTGT GAAAGCAATA AATTATTGAC
Ec Bsr9b       CAATGGATGT TAAACAAAAT GAGATTTAGT GAAAACAATA AATTATTCAC
Ec Bsr9c       CAATGGATGT TAAACAAAAT GAGATTTAGT GAAAACAATA AATTATTCAC
Ec ETEC        CAATGGATGT TAAACANAAT GAGATTTTGT GAANGCNATN NATTATTGNC Consensus   CAATGGATGT TAAACAAAAT GAGATTT-GT GAAA-CAATA AATTATT-AC 201                                                  250
Ec K12, DH5α   TTCGTTTTAG ATTTGTTTAG CTATAATGTT ATACATTCAA ATGACTGAAC
Ec Bsr9b       TTCGTTTTAG ATTTGTTTAG CTATAATGTT ATACATTCAA ATGACTGAAC
Ec Bsr9c       TTCGTTTTAG ATTTGTTTAG CTATAATGTT ATACATTCAA ATGACTGAAC
Ec ETEC        TTCGTTGTAN ATTTGCTNAG CTATAATGTT ATNCATTCAA ATGACTGAAC Consensus   TTCGTT-TAG ATTTG-TTAG CTATAATGTT ATACATTCAA ATGACTGAAC 251        264
Ec K12 DH5α    ATCCTGTAAT TAAA
Ec Bsr9b       ATCCTGTATT TAA-
Ec Bsr9c       ATCCTGTAAT TAA-
Ec ETEC        ATCCTGTNNT TANA Consensus   ATCCTGTAAT TAA-

* SEQ ID NO
```

Fig. 3a

```
                          1                                                           50
Ec K12, DH5α    TTTNCCCGGA  AAAAAATAGG  AAAGGGGGGG  GGGCTAATCG  GCAGGGAAGG  30*
Ec K12, w3110   TNTTNNNCGG  AAAAAAAATNG  AAAGGGGGGG  GGGCTAATCG  GCAGGGAAGG  31*
Ec Bsr9c        --TTTNCCGG  AAAAAAATNG  AAA..GGGGG  GGGCTAATCG  GCAGGGAAGG  32*
Ec (wt) 1       --TNTNCGGA  AAAAAANAGG  AAAGGGGGGG  GGGCTAATCG  GCAGGGAAGG  33*
Ec (wt) 54      -------NCG  GAAAAAAATG  AAA.GGGGGG  GGGCTAATCG  GCAGGGAAGG  34*
Ec (wt) 68      --------CG  GAAAAAAATG  AAA.GGGGGG  GGGCTAATCG  GCAGGGAAGG  35*

Consensus  ----------  -AAAAAA--G  AAA--GGGGG  GGGCTAATCG  GCAGGGAAGG  36*

51                                                          100
Ec K12, DH5α    CCGCCCCGGA  TAGCGGGCGG  CANAAGGAAT  CANAATTTCC  AGGTCAGACG
Ec K12, w3110   CCGCCCCGGA  TAGCGGGCGG  CAGAAGGAAT  CAGAATTTCC  AGGTCAGACG
Ec Bsr9c        CCGCCCCGGA  TAGCGGGCGG  CAGAAGGAAT  CAGAATTTCC  AGGTCAGATG
Ec (wt) 1       CCGCCCCGGA  TAGCGGGCGG  CAGAAGGAAT  CAGAATTTCC  AGGTCAGACG
Ec (wt) 54      CCGCCCCGGA  TAGCGGGCGG  CAGAAGGAAT  CAGAATTTCC  AGGTCAGATG
Ec (wt) 68      CCGCCCCGGA  TAGCGGGCGG  CAGAAGGAAT  CAGAATTTCC  AGGTCAGATG

Consensus  CCGCCCCGGA  TAGCGGGCGG  CAGAAGGAAT  CAGAATTTCC  AGGTCAGA-G 101                                                         150
Ec K12,DH5α     GGCTGCAAGT  TGCAGACCGT  TAAAATCATC  GGNNGGGGTG  TCGTACCACA
Ec K12, w3110   GGCTGCAAGT  TGCAGACCGT  TAAAATCATC  GGTTGGGGTG  TCGTACCACA
Ec Bsr9c        GGCTGCAAGT  TGCAGACCGT  TATAATCATC  GGTTGGGGTG  TCGTACCACA
Ec (wt) 1       GGCTGCAAGT  TGCAGACCGT  TAAAATCATC  GGTTGGGGTG  TCGTACCACA
Ec (wt) 54      GGCTGCAAGT  TGCAGACCGT  TATAATCATC  GGTTGGGGTG  TCGTACCACA
Ec (wt) 68      GGCTGCAAGT  TGCAGACCGT  TATAATCATC  GGTTGGGGTG  TCGTACCACA Consensus  GGCTGCAAGT  TGCAGACCGT  TA-AATCATC  GGTTGGGGTG  TCGTACCACA 151                             180
Ec K12, DH5α    CTTTACCTGC  CGTCAGCCCG  AGATTAA-GTT  -G
Ec K12, w3110   CTTTACCTGC  CGTCAGCCCG  AGATTAA-GTT  -G
Ec Bsr9c        CTTTACCTGC  CGTCAGCCCG  AGATTAA-GTT  -G
Ec (wt) 1       CTTTACCTGC  CGTCAGCCCG  AGATTAAAGTT  TGG
Ec (wt) 54      CTTTACCTGC  CGTCAGCCCG  AGAT-AAAGTT  TGG
Ec (wt) 68      CTTTACCTGC  CGTCAGCCCG  AGAT-AAAGTT  TGG Consensus  CTTTACCTGC  CGTCAGCCCG  AGAT-AA-GTT  -G

* SEQ ID NO
```

Fig. 3b

ABUNDANT, WELL DISTRIBUTED AND HYPERPOLYMORPHIC SIMPLE SEQUENCE REPEATS IN PROKARYOTE GENOMES AND USE OF SAME FOR PROKARYOTE CLASSIFICATION AND TYPING

FIELD AND BACKGROUND OF THE INVENTION

The present invention relates to classification and typing of prokaryotes and, more particularly, to abundant, well distributed and hyperpolymorphic simple sequence repeats in prokaryote genomes and the use of same for prokaryote classification and typing.

Simple sequence repeats (SSRs) are a class of short sequences, usually of 1–6 nucleotides, that are tandemly (i.e., head to tail) repeated from two or three up to a few dozen times at a locus (Vogt 1990). SSRs long have been known to be distributed throughout the genomes of eukaryotes and to be highly polymorphic (Tautz 1989, Weber 1990, Kashi et al. 1990). Polymorphisms arise primarily through slipped-strand mispairing during DNA replication (Strand et al. 1994, Tautz and Schlotterer 1994). There is accumulating evidence that SSRs serve a functional role, affecting gene expression (Kunzler et al. 1995, Kashi et al. 1997, King et al. 1997, Kashi and Soller 1998).

The sequencing of complete genomes of many prokaryotes presented the opportunity to screen such genomes for the existence of SSRs (Field and Wills 1996, 1998), revealing arrays not detected in earlier studies. Recent publication of the complete genome sequence for Escherichia coli (Blattner et al. 1997) provides the basis for characterization of its SSR arrays, both at a gross genomic level and at particular SSR loci.

Present-day approaches for typing of prokaryotes include growth in selective media, binding of specific antibodies, and amplification of DNA using the polymerase chain reaction. For example, conventional methods for detection of E. coli (Vanderzant and Spittstoesser 1992) include enrichment and isolation with selective or indicator media, such as E. coli (EC) broth, lauryl sulfate tryptose 4-methylumbeliferyl-β-D-glucaronic acid broth, eosin methylene blue agar, and McConkey sorbitol agar. Procedures based on use of such media lead to identification of E. coli in a sample and estimation of number, but lack the ability to distinguish among E. coli strains. Hence, the entire process of strain identification remains difficult and time-consuming. Recent methods for identification of E. coli strains use antibodies or nucleic acid sequences that uniquely bind to a particular strain or group of strains. Several methods for immunological detection br biochemical identification of the toxin-producing E. coli strain 0157:H7 have been described (Farmer and Davis 1985, March and Ratnam 1986, Kleanthous et al, 1988, Smith and Scotland 1988, Todd et al. 1988, Karmali 1989, Padbye and Doyle 1991, Tyler et al. 1991). However, these assays do not distinguish among the various members of other serogroups. DNA amplification-based assays have been reported (Karch and Meyers 1989, Pollard et al. 1990, Johnson et al 1990, Johnson et al. 1991, Jackson 1991, Yu and Kaper 1992, Witham et al. 1996), but mostly have limitations including lengthy post-amplification detection protocols or lack of template quantification.

DNA sequence determination, on the other hand, is much more simple and accurate.

There is thus a widely recognized need for, and it would be highly advantageous to have, a simple and rapid DNA sequence based technique for the classification and typing of prokaryotes.

While conceiving the present invention it was assumed that prokaryotes SSRs might be polymorphic and that such polymorphism might be class and type correlated and, if indeed exists, could be used to provide a simple tool for the presently labor-intensive and complicated task of classification and typing of prokaryotes.

While reducing the present invention to practice, length polymorphism was shown at two mononucleotide SSR loci in E. coli. The existence of thousands of SSR arrays in E. coli and in a wide range of other prokaryotes that should exhibit hypervariability is shown as well. Interestingly, these SSR sites exhibit an upper size limit of 12 bp, suggesting selective mechanisms that might impose this size limit.

SUMMARY OF THE INVENTION

According to one aspect of the present invention there is provided a method of classifying or typing a prokaryote to a class or a type, the method comprising the step of characterizing at least one polymorphic simple sequence repeat locus in a genome of the prokaryote and, based on a characterization of the polymorphic simple sequence repeat, classifying or typing the prokaryote to a class or a type.

According to another aspect of the present invention there is provided a pair of polymerase chain reaction primers having a sequence adapted for exponential amplification of a polymorphic simple sequence repeat locus in a genome of a prokaryote.

According to yet another aspect of the present invention there is provided a polymerase chain reaction product derived by amplifying a portion of the genome using the pair of polymerase chain reaction primers described above.

According to still another aspect of the present invention there is provided an allele specific oligonucleotide comprising a sequence of nucleotides adapted for effectively hybridizing only with a specific simple sequence repeat of a polymorphic simple sequence repeat locus in a genome of a prokaryote, under stringent allele specific oligonucleotide hybridization conditions of (i) a hybridization solution of 2×standard sodium citrate (SSC) and 0.1% sodium dodecyl sulfate (SDS); (ii) a hybridization temperature of from 42° C. to Tm −5° C. for 30 minutes to overnight, wherein Tm is estimated as 2×(the number of A plus T residues)+4×(the number of G plus C residues); and (iii) post hybridization washes with 0.75×SSC and 0.1% SDS at a temperature from 42° C. to Tm −5° C. For further details see Bult, C. J., et al., which is incorporated by reference as if fully set forth herein.

According to still an additional aspect of the present invention there is provided a DNA chip comprising a surface and a plurality of allele specific oligonucleotides attached thereto, each of the plurality of allele specific oligonucleotides including a sequence of nucleotides adapted for effectively hybridizing only with a specific simple sequence repeat of a polymorphic simple sequence repeat locus in a genome of a prokaryote, under stringent hybridization conditions as described above. Preferably, the sequence of nucleotides is perfectly complementary to the specific simple sequence repeat.

According to an additional aspect of the present invention there is provided a hybrid of the allele specific oligonucleotide described above and the specific simple sequence repeat.

According to yet additional aspect of the present invention there is provided a primer having a sequence adapted for amplification of a polymorphic simple sequence repeat locus in a genome of a prokaryote.

According to further features in preferred embodiments of the invention described below, characterizing the at least one polymorphic simple sequence repeat locus in the genome of the prokaryote is effected by an allele specific oligonucleotide hybridization.

According to still further features in the described preferred embodiments characterizing the at least one polymorphic simple sequence repeat locus in the genome of the prokaryote is effected by a polymerase chain reaction.

According to still further features in the described preferred embodiments characterizing the at least one polymorphic simple sequence repeat locus in the genome of the prokaryote is effected by a sequencing reaction.

According to still further features in the described preferred embodiments characterizing the at least one polymorphic simple sequence repeat locus in the genome of the prokaryote is effected by a heteroduplex hybridization reaction.

According to still further features in the described preferred embodiments characterizing the at least one polymorphic simple sequence repeat locus in the genome of the prokaryote is effected by single strand conformational polymorphism.

According to still further features in the described preferred embodiments characterizing the at least one polymorphic simple sequence repeat locus in the genome of the prokaryote is effected by restriction fragment length polymorphism.

According to still further features in the described preferred embodiments the at least one polymorphic simple sequence repeat locus is in a non-coding region of the genome.

According to still further features in the described preferred embodiments the prokaryote is of the genus Escherichia.

According to still further features in the described preferred embodiments the prokaryote is *Escherichia coli.*

According to still further features in the described preferred embodiments the prokaryote is of a genus selected from the group consisting of Aquifex, Treponema, Bacillus, Listeria and Mycobacterium.

According to still further features in the described preferred embodiments the prokaryote is selected from the group consisting of *Aquifex aeolicus, Treponema pallidum, Bacillus subtilis, Listeria monocytogenes* and *Mycobacterium tuberculosis.*

According to still further features in the described preferred embodiments the prokaryote is of a genus selected from the group consisting of Haemophilius, Mycoplasma, Helicobacter, Methanococcus, Archaeoglobus and Synechocystis.

According to still further features in the described preferred embodiments the prokaryote is selected from the group consisting of *Haemophilius influenzae, Mycoplasma pneumoniae, Helicobacter pylori, Methanococcus jannaschii, Archaeoglobus fulgidus* and *Synechocystis* sp. PCC6803.

The present invention successfully addresses the shortcomings of the presently known configurations by providing a highly polymorphic genetic tool for efficient rapid and accurate taxonomy of prokaryotes, which can be used for ultimate classification and typing.

BRIEF DESCRIPTION OF THE DRAWINGS

The invention herein described, by way of example only, with reference to the accompanying drawings, wherein:

FIGS. 3*a–b* show DNA sequence alignments for complementary DNA strands for two loci bearing mononucleotide repeat polymorphisms in strains of *E. coli*. PCR products were sequenced using the dideoxy-chain termination method, and aligned using the "Pile-up" program of the Genetics Computing Group version 9, default option for routine "pile-up", wherein consensus sequences determined by the routine called "pretty" was set so that any difference among sequences was regarded as lack of consensus. SSR arrays are shown in bold letters, and the TATA box where shown, is underlined. FIG. 3*a*—Poly-C tract of ycgw. FIG. 3*b* Poly-G and Ploy-T tracts of yaiN.

DESCRIPTION OF THE PREFERRED EMBODIMENTS

Figure 1A:
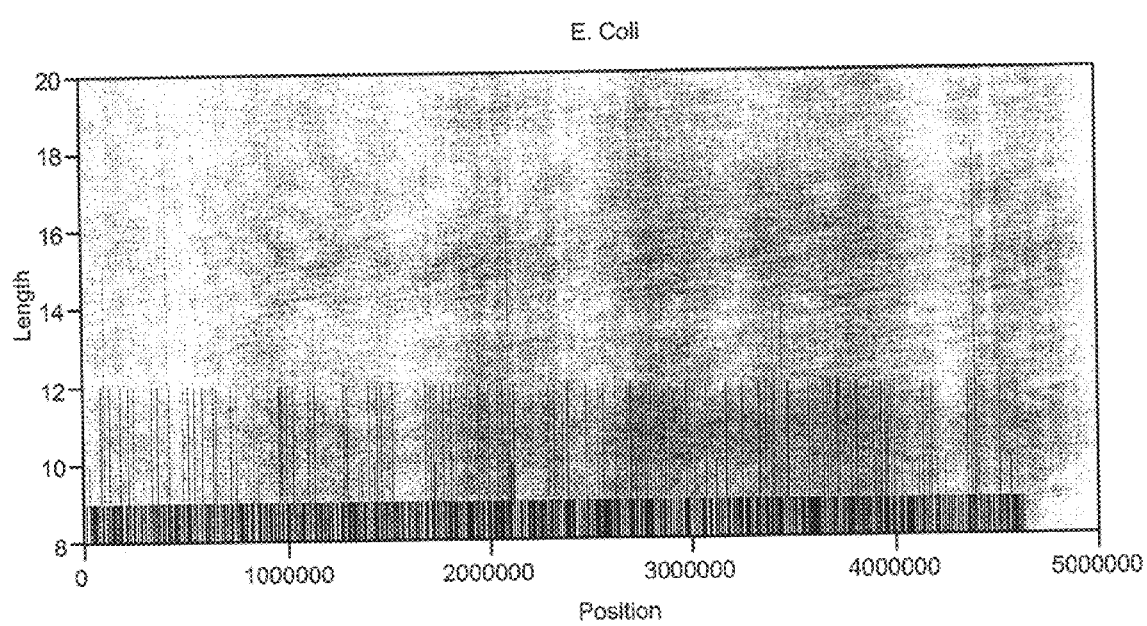
FIGS. 1*a–d* show the lengths of microsatellite arrays at given positions (bp) in selected, completely sequenced genomes of *Escherichia coli, Bacillus subtilus, Archaeoglobus fulgidus* and *Saccharomyces cerevesiae* chromosome No. 7, respectively.
Figure 1B:
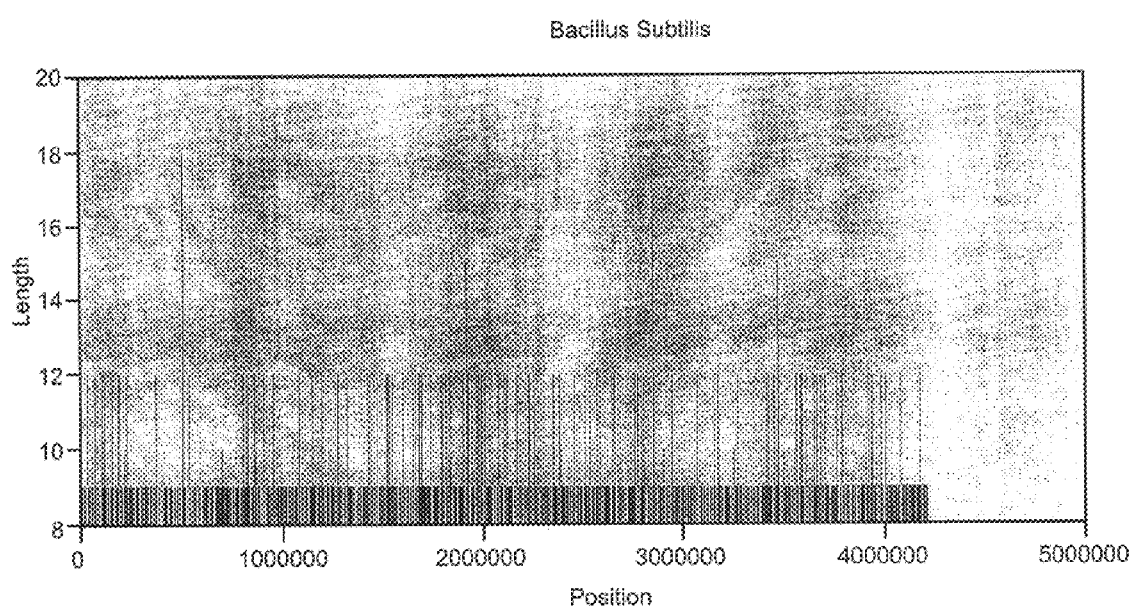
Figure 1C:
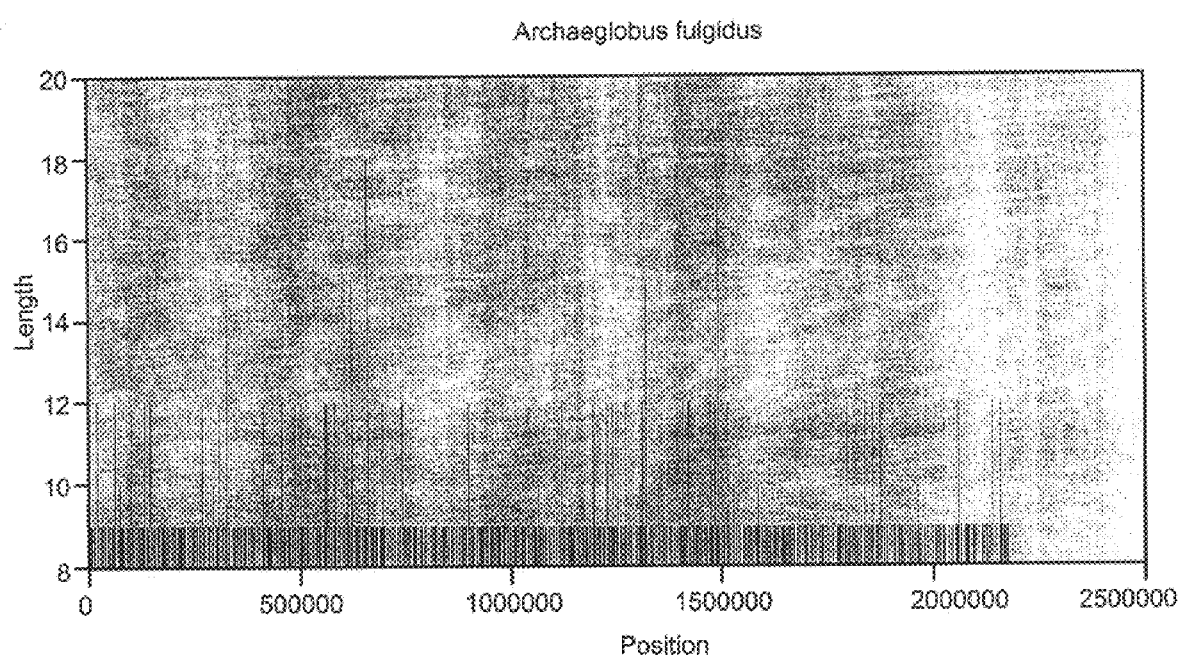
Figure 1D:
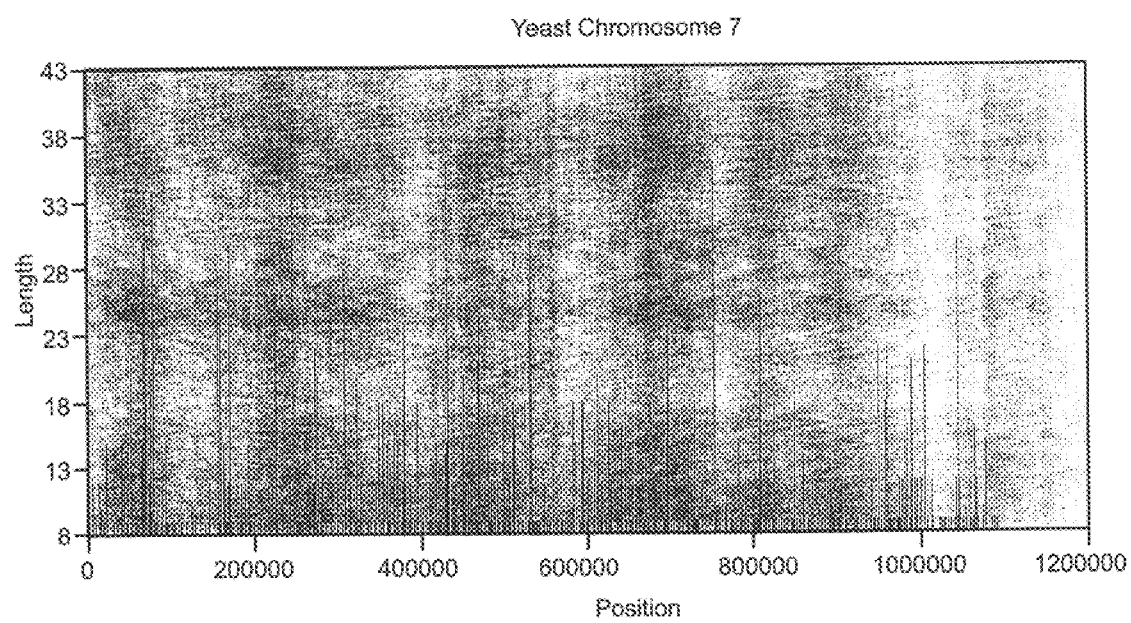

The present invention is of a method of classifying or typing a prokaryote to a class or a type which can be used in research and medical and food safety diagnostics. Specifically, the present invention can be used to type strains and substrains of prokaryotes into classes and types according to the established taxonomy by associating specific morphs of highly polymorphic simple sequence repeat loci with such classes and types. The invention is further of articles of manufacture, such as DNA chips, and other single nucleotide polymorphism (SNP)-based compounds, typically oligonucleotides or primers, useful in efficiently implementing the method according to the present invention for research and medical and food safety diagnostics.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Although the existence of simple sequence repeat (SSR) DNA arrays in eukaryotic genomes long has been known, their existence in prokaryotic genomes only recently has been recognized. While reducing the present invention to practice, analysis of the published DNA sequence of *E. coli* strain K12 revealed tens of thousands of well distributed SSR arrays. PCR primer pairs were then developed for several SSR loci, and polymorphisms was found at two mononucleotide SSR loci. These results suggest that SSRs provide a ready source of genetic variability to be exploited by evolution and which is useful for a variety of applications as further detailed hereinunder. Polymorphisms differentiate non-pathogenic and pathogenic groups of *E. coli* strains, suggesting the utility of SSR typing for rapid, PCR- or oligonucleotide-based detection of pathogenic strains for diagnostics (medical and food safety) or for epidemiological studies. Analysis of published complete genome sequences of *E. coli* and 10 additional prokaryotes showed the existence of thousands of mono-, di-, tri-, and tetranucleotide microsatellite arrays, mostly in non-coding sequences. A general limit of 12 nucleotides in SSR array size was observed, suggesting the effect of a selective mechanism limiting array size. Because SSR polymorphisms in promoter regions could alter gene expression, it is inferred that such polymorphisms are an important factor in prokaryotic evolution and could be used by biotechnologists to purposefully "fine-tune" gene regulation in a microorganism of interest.

SSR content of *E. coli*: SSRs in *E. coli*, a gram-negative bacterium of interest as a model species and as a human pathogen, were characterized. The reslits show that SSR arrays in *E. coli* are numerous and diverse-in terms of core sequence and repeat number. As further discussed below, SSRs in *E. coli* are also polymorphic. Findings of previous studies reflect the growing understanding of SSRs in *E. coli*. SSR regions in *E. coli* were thought to be very rare, limited to only a few dinucleotide SSRs with a maximum of five repeat units per locus (van Belkum et al. 1998). Field and Wills (1998) presented data showing the existence of hundreds of thousands of mononucleotide SSRs in *E. coli*, and mentioned SSRs with core lengths varying from 1 to 6 bp.

Polymorphism ofSSRs in *E. coli*: The data collected while reducing the present invention to practice show repeat number variation at two out of four mononucleotide SSR loci examined in *E. coli*, and suggest that mononucleotide SSR loci may prove a source of thousands of polymorphisms for marking its genome. In contrast, polymorphisms were not observed at SSR loci with two or more nucleotide core sequences, however, this may be due to the small sample size employed.

Genomic locations of SSRs in *E. coli*: The findings reported herein indicate that SSR arrays in *E. coli* tend to be located 5' or 3' relative to coding sequences of genes. Similarly, in eukaryotes, arrays of certain types of repetitive DNA have been located to the 5' or 3' flanking regions of genes. These repeats may be involved in nucleosome organization, recombination, or regulation of gene expression or gene product activity (Tripathi and Bramachani 1977, Kashi et al. 1997, King et al. 1997, Kashi and Soller 1988). This also has been inferred for *E. coli* (Rosenberg et al. 1994). Sections of microbial genomic DNA bearing visibly different frequencies of tetranucleotide repeats than other parts of the genome contained ribosomal RNA, bacteriophage, or undefined coding regions (Noble et al. 1998).

SSRs in other prokaryotes: The presence of SSRs in genomes of several prokaryotes has been demonstrated in recent studies, and some SSR loci have been shown to exhibit length polymorphisms (reviewed by van Belkum et al. 1998), yet these SSRs are restricted to protein coding sequences. Variation was shown in trinucleotide repeats of very large array size in simple eukaryotes (Field and Wills 1996). The existence of mononucleotide microsatellites was subsequently shown in eight prokaryotic genomes, however, polymorphism was not persuaded or anticipated (Field and Wills 1998). For genomes surveyed in both studies, the results shown herein agree very closely with those of Field and Wills (1998). The existence of SSR arrays with 1–6 bp core sequences in 10 additional prokaryotes, including four (*Aquifex aeolicus, Treponema pallidum, Bacillus subtilis*, and *Mycobacterium tuberculosis*) not previously surveyed is reported herein.

Thousands of SSRs with a range of core repeat sizes were observed in all genomes examined (see Table 1 in the Examples section that follows). The results presented herein differ in these respects from certain earlier findings. van Belkum et al. (1998) reported that only dinucleotide SSR candidates were detected in *Methanococcus jannaschii*, while SSRs with core sequences of one to six nucleotides observed. van Belkum et al. (1997b) found only 18 potential SSRs in the genome of *Hemophilus influenzae*, and Scherer and van Belkum (unpublished data cited in Van Belkum et al. 1998) found no perfectly repetitive DNA sequence motifs in the genome of *Mycobacterium tuberculosis*. Differences in the search algorithms for the software packages that the respective groups used may explain the different findings.

The algorithm used herein, which is available at http://www.technion.ac.il/pub/supported/biotech. In the first step, the user defines the minimum length and number of repeats of the core sequence, and hence, the minimum length of the SSR sought. The program then scans the genomic sequence at issue. When it reads a motif suiting the parameters specified, it checks whether this motif is contained within a repeated sequence by comparing its sequence with that of nucleotides following it. If the motif is indeed repeated, the program counts the number of repeats. The program will write the core sequence, the number of repeats, and the genomic location of the SSR in an output file. The program then will continue to move through the genomic sequence at issue, continuing in such fashion until the entire genome has been read and evaluated. This differs from earlier programs of similar intent because it both searches for all SSRs with repeat lengths up to a defined number of base pairs in length and records the genomic location of each repeat motif found.

Size limit of SSR arrays: Analysis of SSR tracts in genomic DNA sequences for *E. coli* and a wide variety of other prokaryotes shows that SSR array length is small relative to eukaryotes. The length of SSR tracts is determined by interacting processes of mutation and selection. Mutation at SSR loci is believed to be the consequence of slipped-strand mispairing during DNA replication (Strand et al. 1994, Tautz and Schlotterer 1994). The tertiary structure of repetitive DNA allows mismatching of neighboring repeats, and depending on the strand orientation, repeats can be inserted or deleted during DNA polymerase-mediated DNA duplication (Coggins and O'Prey 1989, Hauge and Litt 1993, Chiurazzi et al. 1994). High mutation rate at SSRs result when the DNA repair system is non-functional. The resulting mutations are not always repaired by DNA mismatch repair mechanisms (Strand et al. 1993). Additionally, polyAC/TG repeats are destabilized by mutations that induce SOS response in *E. coli* (Morel et al. 1998).

The data set presented herein exhibits certain repeat array lengths more frequently than others (see Table 1 in the Examples section that follows). Frequencies of particular SSR array lengths in *E. coli* do not decrease monotonically from 3 to 18. There are more arrays of 9 bp in length than of 7 or 8, and more of 12 bp in length than of 10 or 11. Array lengths with odd numbers of nucleotides greater than five are less common than arrays with comparable, even numbers of nucleotides. These observations run counter to expectations due to particular SSR sequences arising by chance.

It is hypothesized that the frequencies of arrays exhibiting particular length are, in part, the consequence of the number of ways in which those particular repeat lengths can arise. An SSR repeat tract with a length of twelve bp can arise following five types of mutations: a mononucleotide may be repeated 12 times, a dinucleotide six times, a trinucleotide four times, a tetranucleotide three times, or a hexanucleotide twice. However, certain SSR structures of 12 bp in length are more common than others. In E. coli No tracts were found where a single nucleotide was repeated 12 times, one where a dinucleotide was repeated six times, 54 where a trinucleotide was repeated four times, 47 where a tetranucleotide was repeated three times, and none where hexanucleotides were repeated twice. That SSR arrays of 12 bp in length occur 102 times, while arrays of 10 bp in length occur only 21 times, may be explained, in part, by there being only three ways by which mutation will give rise to an array of 10 bp; i.e., a mononucleotide may be repeated 10 times (one occurrence), a dinucleotide may be repeated five times (20 occurrences), or a pentanucleotide may be repeated twice (none). SSR arrays of nine nucleotides can arise two ways, either a mononucleotide repeated nine times (17 occurrences), or a trinucleotide can be repeated three times (2,013 occurrences). SSR arrays greater than 12 bp in length are not expected in the genome by chance alone, yet a few occur (two occurrences of a trinucleotide repeated five times, one of a tetranucleotide repeated four times, and two of a hexanucleotide repeated three times). Hence, not all mutations are equally likely, or a selective factor must be invoked to explain frequencies of SSRs of different structures. Although each prokaryote has its own distribution of SSR array sizes (Table 1, FIG. 1), in general, the upper limit for the size of SSR arrays is 12 bp. This suggests that the tendency for repeat length at a locus to rise via mutation is counteracted by selection, which affects the distribution of combinations of core length and repeat number, and which holds total SSR array length under 12 bp. This supports the hypothesis (Kashi et al 1997, King et al. 1997) that some SSRs provide a source of variation that affects gene expression and, hence, is subject to selection.

Screening of SSRs among strains of E. coli showed seven sites exhibiting no polymorphism. The rate of mutations giving rise to SSR variation should be the same across a genome. Therefore, wherever there is a site that is totally conserved, one may infer that selection is operating at that locus. Hence, it is believed that monomorphic SSR sites are under strong selection, which will not tolerate mutations in these loci.

The distribution of SSR array sizes in yeast (Table 1, FIG. 1), a eukaryote, is different from those in prokaryotes. The distribution of SSR sizes includes longer core sequences and larger repeat numbers than in prokaryotic genomes. The process of generating polymorphism of SSRs, slipped strand replication, is expected to have roughly similar frequency and effects in prokaryotes and eukaryotes. The difference in the distribution of SSR array sizes may be attributable to a relaxed selective regime within eukayotic genomes, which tolerate the presence of more "junk" DNA than prokaryotic genomes.

Practical utility of SSR polymorphisms: SSR polymorphism offers a useful tool for analysis of prokaryotic genomes. SSRs are widely used as a means for developing DNA fingerprints for eukaryotes. To characterize SSR polymorphisms in eukaryotes, large fragments have to be sized accurately, by DNA sequencing gels or by electrophoresis of PCR amplification products, necessarily involving the technical question of whether a gel supported accurate electrophoresis and thereby provided reliable results. In contrast, polymorphic mononucleotide sites that were found in E. coli exhibit 1 to 4 bp size differences. These small numbers of repeats are well suited for the development of SSR allele-specific oligonucleotides (ASOs). There are many existing and future methods for developing ASOs or SNPs that may be used to identify polymorphisms of SSRs. These ASOs or SNPs may be used as PCR primers, or as hybridization probes that can be spotted on the surface of a DNA chip for rapid, automated characterization of variation at a set of given loci for each E. coli genome. Upon preparation of PCR probes or a DNA chip, polymorphisms of prokaryotic SSRs may be screened to support a variety of research and diagnostic applications.

It is especially interesting that E. coli is part of the normal human microflora, but there are pathogenic strains that have to be distinguished and rapidly detected. The use of SNPs, single nucleotide polymorphisms, is the preferrod rising technique that can be used to automatically soreen polymorphism. Affymetix, Inc. has developed a DNA chip for implementing that technique. To this end, see U.S. Pat. No. 5,843,655 for "Methods for testing oligonucleotide arrays"; U.S. Pat. No. 5,837,832 for "Arrays of nucleic acid probes on biological chips"; U.S. Pat. No. 5,834,758 for "Method and apparatus for imaging a sample on a device"; U.S. Pat. No. 5,831,070 for "Printing oligonucleotide arrays using deprotection agents solely in the vapor phase"; U.S. Pat. No. 5,770,722 for "Surface-bound, unimolecular, double-stranded DNA"; U.S. Pat. No. 5,770,456 for "Cyclic nucleic acid and polypeptide arrays"; U.S. Pat. No. 5,753,788 for "Photolabile nucleoside protecting groups"; U.S. Pat. No. 5,744,305 for "Arrays of materials attached to a substrate"; U.S. Pat. No. 5,733,729 for "Computer-aided probability base calling for arrays of nucleic acid probes on chips"; U.S. Pat. No. 5,710,000 for "Capturing sequences adjacent to Type-IIs restriction sites for genomic library mapping"; U.S. Pat. No. 5,631,734 for "Method and apparatus for detection of fluorescently labeled materials"; U.S. Pat. No. 5,599,695 for "Printing molecular library arrays using deprotection agents solely in the vapor phase"; and U.S. Pat. No. 5,593, 839 for "Computer-aided engineering system for design of sequence arrays and lithographic masks", which are incorporated by reference as if fully set forth herein.

The polymorphic and small SSRs (12 nucleotides or less) reported herein can take advantage in combining the DNA chip technology with the ASO technology for their detection. However, as other rapid methods may be developed, the scope of the present invention is not limited to DNA chip technology.

Screenings of SSR variation may provide the basis for rapid and sensitive identification of E. coli strains, and sometimes may prove advantageous over existing serotyping or molecular genetic methods, distinguishing strains or subdividing strains to subgroups. For example, SSR variation may prove useful for rapidly and sensitively characterizing pathogenic strains of E. coli, such as O157:H7, from more common strains. Similarly, knowledge of SSR variation in other pathogenic microbes, such as Haemophilus influenzae (van Belkum et al. 1997a), Candida albicans (Bretagne et al. 1997), Bacteroidesfragilis and B. thetaiotaomicron (Claros et al. 1997), and Helicobacter pylon (Marshall et al. 1996), might be applied for rapid detection and strain characterization.

SSRs can be screened to determine to what extent molecular variation gives rise to phenotypic variation. For example, SSR variability poses clear implications with regard to virulence. Motifs of SSRs have been found within suspected or confirmed virulence genes of Hemophilus influenzae (Karlin et al. 1996); Neisseria sp., Hemophilus parainfluenzae, and Moraxella catarrhalis (Peak et al. 1996), and repeat number variation seems to be related to modulation of the expression of virulence factors. Contingency genes containing SSRs exhibit high mutation rates, allowing the bacterium to respond rapidly upon encountering challenging environmental conditions (Moxon et al. 1994). Location of SSR repeat arrays by computerized search of the genomic sequence and localization of such arrays with regard to expressed genes, as reported herein, could provide a basis for searching for new virulence-related loci in E. coli.

SSR polymorphism can be used for epidemiological purposes, for example, to determine whether a pathogenic E. coli strain detected in a patient matches a potential source of a given disease outbreak. SSRs have been used as markers for such purposes for several pathogenic microbes. For example, repetitive DNA elements of Mycobacterium tuberculosis have been used for efficient strain tracking (Van Soolingen et al. 1993). Epidemiologically informative microsatellite DNA polymorphisms have been observed in different strains of Helicobacter pylon (Marshall et al. 1996). SSR variation has been used to identify the strains of Haemophilus influenzae isolated from different patients (van Belkum et al. 1997a). To demonstrate a similar approach in E. coli, a series of allelic SSR markers distinguishing relevant strains can be developed. The observation reported herein of polymorphism within the B strain between SR9b and SR9c suggests that SSR markers might even prove capable of resolving variation within strains.

Many SSR arrays are found in the promoter regions of genes, affecting the expression of genes in a way tolerated by the host bacterium (Kashi et al. 1997, King et al. 1997). The results shown herein represent a 100 kb sample of the E. coli genome, and should be representative of the entire genome thereof. Constancy of dinucleotide relative abundance profiles has been shown over multiple 50 kb disjoint contigs within the same genome in E. coli and 14 other prokaryotes (Karlin et al. 1997). This source of phenotypic variation can be exploited not only by natural selection, but also by biotechnologists to manipulate bacterial genomes to express a desired phenotype.

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations.

Various methods are known in the art which may be used to detect and characterize specific nucleic acid sequences and sequence changes. Nonetheless, as nucleic acid sequence data of the human genome, as well as the genomes of pathogenic organisms accumulates, the demand for fast, reliable, cost-effective and user-friendly tests for specific sequences continues to grow. Importantly, these tests must be able to create a detectable signal from a very low copy number of the sequence of interest. The following discussion examines three levels of nucleic acid detection currently in use: (i) signal amplification technology for detection of rare sequences; (ii) direct detection technology for detection of higher copy number sequences; and (iii) detection of unknown sequence changes for rapid screening of sequence changes anywhere within a defined DNA fragmet.

Signal amplification technology methods for amplifcation:

The "Polymerase Chain Reaction" (PCR) comprises the first generation of methods for nucleic acid amplification. However, several other methods have been developed that employ the same basis of specificity, but create signal by different amplification mechanisms. These methods include the "Ligase Chain Reaction" (LCR), "Self-Sustained Synthetic Reaction" (3SR/NASBA), and "Qβ-Replicase" (Qβ).

The polymerase chain reaction (PCR), as described in U.S. Pat. Nos. 4,683,195 and 4,683,202 to Mullis and Mullis et al., describe a method for increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

The ligase chain reaction (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. Segev, PCT Public. No. W09001069 A1 (1990). However, because the four oligonucleotides used in this assay can pair to form two short ligatable fragments, there is the potential for the generation of target-independent background signal. The use of LCR for mutant screening is limited to the examination of specific nucleic acid positions.

The self-sustained sequence replication reaction (3SR) (Guatelli et al., Proc. Natl. Acad. Sci., 87:1874–1878, 1990, with an erratum at Proc. Natl. Acad. Sci., 87:7797, 1990) is a transcription-based in vitro amplification system (Kwok et al., Proc. Natl. Acad. Sci., 86:1173–1177, 1989) that can exponentially amplify RNA sequences at a uniform temperature. The amplified RNA can then be utilized for mutation detection (Fahy et al., PCR Meth. Appl., 1:25–33, 1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200–300 base pairs).

In Q-Beta (Qβ), a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37° C.). This prevents the use of high temperature as a means of achieving specificity as in the LCR, the ligation event can be used to detect a mutation at the junction site, but not elsewhere.

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55° C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

The basis of the amplification procedure in the PCR and LCR is the fact that the products of one cycle become usable templates in all subsequent cycles, consequently doubling the population with each cycle. The final yield of any such doubling system can be expressed as: $(1+X)^n=y$, where "X" is the mean efficiency (percent copied in each cycle), "n" is the number of cycles, and "y" is the overall efficiency, or yield of the reaction (Mullis, PCR Methods Applic., 1:1, 1991).

Many applications of nucleic acid detection technologies, such as in studies of allelic variation, involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence.

A similar 3'-mismatch strategy is used with greater effect to prevent ligation in the LCR (Barany, PCR Meth. Applic., 1:5, 1991). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

Direct detection technology:

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats. Two examples are the "Cycling Probe Reaction" (CPR), and "Branched DNA" (bDNA).

The cycling probe reaction (CPR) (Duck et al., BioTech., 9:142, 1990), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA (bDNA), described by Urdea et al., Gene 61:253–264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

Detection of unknown sequence changes:

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet unknown mutations within specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

For detection of single-base or length differences between like sequences, the requirements of the analysis are often at the highest level of resolution. For cases in which the position of the nucleotide or nucleotides in question is known in advance, several methods have been developed for examining single base changes without direct sequencing. For example, if a mutation of interest happens to fall within a restriction recognition sequence or between restriction recognition sequences when, a change in the pattern of digestion or gel migration can be used as a diagnostic tool (e.g., restriction fragment length polymorphism (RFLP) analysis.

Single point mutations have been also detected by the creation or destruction of RFLPs. Mutations are detected and localized by the presence and size of the DNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817, 1990). However, this method requires the use of osmium tetroxide and piperidine, two highly noxious chemicals which are not suited for use in a clinical laboratory.

If the change is not in a recognition sequence, then allele-specific oligonucleotides (ASOs), can be designed to hybridize in proximity to the unknown nucleotide, such that a primer extension or ligation event can be used as the indicator of a match or a mis-match. Hybridization with radioactively labeled allelic specific oligonucleotides (ASO) also has been applied to the detection of specific point mutations (Conner et al., Proc. Natl. Acad. Sci., 80:278–282, 1983). The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes (Vogelstein et al., N. Eng. J. Med., 319:525–532, 1988; and Farr et al., Proc. Natl. Acad. Sci., 85:1629–1633, 1988), and gsp/gip oncogenes (Lyons et al., Science 249:655–659, 1990). Because of the presence of various nucleotide changes in multiple positions, the ASO method requires the use of many oligonucleotides to cover all possible mutations.

With either of the techniques described above (i.e., RFLP and ASO), the preoise location of the suspected mutation must be known in advance of the test. That is to say, they are inapplicable when one needs to detect the presence of a mutation of an unknown character and position within a gene or sequence of interest.

Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G-C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463–475, 1990). Attaching a GC clamp to one primer is critical to ensure that the amplified sequence has a low dissociation temperature (Sheffield el al., Proc. Natl. Acad. Sci., 86:232–236, 1989); and Lerman and Silverstein, Meth. Enzymol., 155:482–501, 1987). Modifications of the technique have been developed, using temperature gradients (Wartell et al, Nucl. Acids Res., 18:2699–2701, 1990), and the method can be also applied to RNA:RNA duplexes (Smith et al., Genomics 3:217–223, 1988).

The long running time of DGGE was shortened in a modification of DGGE called constant denaturant gel electrophoresis (CDGE) (Borrensen el al., Proc. Natl. Acad. Sci. USA 88:8405, 1991). CDGE requires that gels be performed under different denaturant conditions in order to reach high efficiency for the detection of unknown mutations.

A technique analogous to DGGE, termed temperature gradient gel electrophoresis (TGGE), uses a thermal gradient rather than a chemcial denaturant gradient (Scholz, el al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA. Therefore scanning of large gene segments requires the use of multiple PCR products prior to running the gel.

Another common method, called "Single-Strand Conformation Polymorphism" (SSCP) was developed by Hayashi, Sekya and colleagues (reviewed by Hayashi, PCR Meth. Appl., 1:34–38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874–879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

The dideoxy fingerprinting (ddF) is another technique developed to scan genes for the presence of unknown mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresised on nondenaturing polyacrylamide gels to detect alterations in mobility of the termination segments as in SSCP analysis.

According to one aspect of the present invention there is provided a method of classifying or typing a prokaryote to a class or a type. The method according to the present invention is effected by characterizing at least one polymorphic simple sequence repeat locus in a genome of the prokaryote and, based on a characterization of the polymorphic simple sequence repeat, classifying or typing the prokaryote to a class or a type.

It is shown hereinunder in the Examples section that simple sequence repeat loci are highly abundant among various prokaryotes of different genera. It is further shown hereinunder in the Examples section that simple sequence repeat loci can be highly polymorphic within strains and substrains of the same prokaryote species. The method according to the present invention takes advantage over these findings to provide an effective, readily implementable, rapid and accurate tool for classifying or typing a prokaryote to a class or a type.

As described above, the art of molecular biology provides a plurality of experimental protocols and devices dedicated at characterizing sequences. Many such protocols and devices were developed to assist in rapid characterization of polymorphic loci in eukaryotes, human beings in particular, typically to assist in pre- and postnatal detection and/or diagnosis of genetic disorders.

These methods and devices can be efficiently implemented in combination with the method according to the present invention to assist in characterizing polymorphic simple sequence repeat loci in the genome prokaryotes.

Characterizing polymorphic simple sequence repeat loci in the genome prokaryotes can, for example, be effected by any one of the methods described hereinabove. Yet other methods can also be applicable for such characterization.

Characterizing polymorphic simple sequence repeat loci in the genome prokaryotes according to the present invention can be effected, for example, by an allele specific oligonucleotide hybridization.

As further detailed hereinabove, allele specific oligonucleotide hybridization is based on the ability of nucleic acid sequences to form specific hybrids with nucleic acids complementary thereof. When short sequences of up to about 50 nucleotides are let to hybridize, one can, by appropriately selecting the hybridization conditions, control the effectiveness of the hybridization to a degree which is sensitive to minute sequence alterations present between the hybridizing sequences, even to a degree of a single point mutation or mismatch. In other words, for sequences shorter than 50, preferably shorter than 40, more preferably shorter than 30, most preferably in the range of 8 to 20 nucleotides in length, hybridization conditions are providable, so as to allow only complete matching strands to hybridize, whereas as little as a single point mutation prevents such hybridization.

The hybridization conditions selected for allele specific oligonucleotide hybridization are very much dependent on the sequence of the hybridizing strands. These conditions are typically accomplished for specific sequences by changing the temperature underwhich hybridization takes place. Since a single mismatch between hybridizing strands lowers the melting temperature (Tm, the temperature in which 50% of the strands are found as hybrids) thereof by about 2.5° C., controlling the hybridization temperature provides an effective means for controlling allele specific oligonucleotide hybridization. When a plurality of hybridizations are carried out simultaneously, so that it is not practical to control the temperature, control of the length of the hybridizing sequences is preferably exercised, to thereby bring the $T_m$s of all hybridizing pairs to a close range.

Thus, according to the present invention there is provided an allele specific oligonucleotide comprising a sequence of nucleotides adapted for effectively hybridizing only with a specific simple sequence repeat of a polymorphic simple sequence repeat locus in a genome of a prokaryote, under stringent allele specific oligonucleotide hybridization conditions of (i) a hybridization solution of 2×standard sodium citrate (SSC) and 0.1% sodium dodecyl sulfate (SDS); (ii) a hybridization temperature of from 42° C. to Tm −5° C. for 30 minutes to overnight, wherein Tm is estimated as 2×(the number of A plus T residues)+4×(the number of G plus C residues); and (iii) post hybridization washes with 0.75×SSC and 0.1% SDS at a temperature from 42° C. to Tm −5° C.

Further according to the present invention there is provided a DNA chip comprising a surface and a plurality of allele specific oligonucleotides attached thereto. Each of the plurality of allele specific oligonucleotides includes a sequence of nucleotides adapted for effectively hybridizing only with a specific simple sequence repeat of a polymorphic simple sequence repeat locus in a genome of a prokaryote, under the stringent hybridization conditions described above.

In a preferred embodiment of the present invention, the sequence of nucleotides selected for the allele specific oligonucleotides according to the present invention is perfectly complementary to their respective specific simple sequence repeats.

As further detailed hereinabove, another widely accepted method in molecular biology is the polymerase chain reaction (PCR) in which primers having the 3' end thereof facing each other yet which are complementary to different strands of a double stranded nucleic acid molecule are employed to provide for exponential amplification of a portion of the double stranded nucleic acid molecule defined by the boundaries of the primers by a cycled physical/enzymatic reaction of three substeps: primers annealing (physical), primers elongation (enzymatic) and primers denaturation (physical), effected by cycling the reaction temperature.

Since its introduction, numerous protocols have been developed in which the polymerase chain reaction has been successfully used for detection of sequence polymorphisms, including repeats, e.g., triple repeats, in the genome of human beings.

Thus, according to another aspect of the present invention there is provided a pair of polymerase chain reaction primers having a sequence adapted for exponential amplification of a polymorphic simple sequence repeat lows in a genome of a prokaryote. According to yet another aspect of the present invention there is provided a primer having a sequence adapted for amplification of a polymorphic simple sequence repeat locus in a genome of a prokaryote. Such primers have a length of between 10 and 40 nucleotides and are typically flanking the polymorphic site. Examples of such primers are provided in the Examples section hereinunder. Such primers can be used to provide polymerase chain reaction products of a polymorphic length depending on the specific genome, a portion thereof they are designed to amplify. The morph of the product thus obtained can be identified by one of a plurality of protocols, including size separation such as gel electrophoresis and sequence determination via DNA sequencing using for example the dideoxy sequencing protocol, via allele specific hybridization as described above or via other methods, some of which are further detailed herein.

As further detailed hereinabove, the formation of heteroduplexes can be employed for detection of polymorphism in nucleic acids, e.g., as effected by TGGE or DGGE. Thus, according to an embodiment of the present invention characterizing the at least one polymorphic simple sequence repeat locus in the genome of the prokaryote is effected by a heteroduplex hybridization reaction.

As further detailed hereinabove, single strand conformational polymorphism (SSCP) can be employed for detection of polymorphism in nucleic acids. Thus, according to an embodiment of the present invention characterizing the at least one polymorphic simple sequence repeat locus in the genome of the prokaryote is effected by single strand conformational polymorphism.

As further detailed hereinabove, restriction fragment length polymorphism (RFLP) can be employed for detection of polymorphism in nucleic acids. Thus, according to an embodiment of the present invention characterizing the at least one polymorphic simple sequence repeat locus in the genome of the prokaryote is effected by restriction fragment length polymorphism.

According to a presently preferred embodiment of the present invention the polymorphic simple sequence repeat loci employed for classification or typing using the method of the present invention are located is in a non-coding region of the genome of the prokaryotes analyzed. Such a location is presently preferred because the degree to which variability is permitted in such regions is to a much greater extent higher in evolutionary terms. It is well known that while coding region mutations are in most cases selected against, no such effective selection pressure is imposed on mutations present in non-coding regions.

As used herein in the specification and in the claims section below, the term "non-coding" refers to regions in the prokaryotic genome that do not include direct information for the synthesis of proteins, i.e., are not a part of a translated sequence.

The polymorphic simple sequence repeat loci employed for classification or typing using the method of the present invention are typically 12 bp long or less and are composed of single, di-, tri- tetra-penta- or hexanucleotide repeats. Thus, the number of repeats can range, in most cases, from 2 to 12. Longer repeats are not excluded, yet are shown herein to be much less abundant in prokaryotes.

The invention described herein is taken not to be limited to any prokaryote genus or species in particular. Indeed, as further Exemplified hereinunder, any prokaryote tested so far was shown to abundantly include simple sequence repeats.

Thus, the prokaryote can be of the genus Escherichia, such as *Escherichia coli*. It can also be from the genera Aquifex, Treponema, Bacillus, Listeria or Mycobacterium, such as *Aquifex aeolicus, Treponema pallidum, Bacillus subtilis, Listeria monocytogenes* and *Mycobacterium tuberculosis*, respectively. Yet it can also be from any other genera, such as, but not limited to, Haemophilius, Mycoplasma, Helicobacter, Methanococcus, Archaeoglobus or Synechocystis, for example, *Haemophilius influenzae, Mycoplasma pneumoniae, Helicobacter pylori, Methanococcus jannaschii, Archaeoglobus fulgidus* or Synechocystis sp. PCC6803.

It will be appreciated that the scope of the present invention is not limited to the polymorphism detection methods described herein, and that other polymorphism detection methods can be effectively employed to implement the invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., Molecular Cloning—A Laboratory Manual, Cold Spring Harbor Laboratory, Cold Spring Harbor, N.Y. (1989). The manual is hereinafter referred to as "Sambrook". Other general references are provided throughout this document. The procedures therein are believed to be well known in the art and are provided for the convenience of the reader. All the information contained therein is incorporated herein by reference.

Experimental Methods

Genomic Sequence Analysis:

A DNA sequence analysis software in the programming language C that screens entire genomes for SSRs of 1–6 bp core length and reports core sequence, number of repeats, and genomic position was used for gnomic sequence analysis. This DNA sequence analysis software is available for downloading from http://www.technion.ac.il/pub/supported/biotech.

The complete genomic sequence of *Escherichia coli* (Blattner et al. 1997) was obtained by ftp from GenBank, and screened for the occurrence of SSRs, their core sequence, number of repeats, and genomic locations. The identity of genes in the region and the locations of the SSRs with regard to coding and non-coding elements of such genes was assessed by use of the BLAST DNA sequence analysis program (available at http://www.ncbi.nlm.nih.gov/blast.

Complete genome sequences of *Aquifex aeolicus* (Deckert et al. 1998), *Treponema pallidum* (Fraser et al. 1998), *Haemophilus influenzae* (Fleischmann et al. 1995), *Mycoplasma pneumoniae* (Himmelreich et al. 1996), *Bacillus subtilis* (Kunst et.al. 1997), *Helicobacter pylori* 26695 (Tomb et al. 1997), *Methanococcus jannaschii* (Bult et al. 1996), *Archaeoglobus fulgidus* (Klenk et al 1997), Synechocystis sp. PCC6803 (Kaneko and Tabata 1997), and *Saccharomyces cerevesiae* chromosome VII (Tettelin et al. 1997) were obtained by fip from GenBank.

Characterization of *E. coli* Microsatellites:

PCR Amplification Primers:

Nine SSR loci of *E. coli* were selected for detailed analysis. The forward (F) and reverse (R) PCR primer sequences for the loci examined are as follow:

ycgW: F, 5'-GATTTTGCATATGAGTATATTAC-3' (SEQ ID NO:1); R, 5'-TTAATTACAGGATGTTCAGTC-3' (SEQ ID NO:2).

yaiN: F, 5'-AATTTATCCGGTGAATGTGGT-3' (SEQ ID NO:3); R, 5'-CAACTTAATCTCGGGCTGAC-3' (SEQ ID NO:4).

YjiD: F, 5'-TACATGGCTGATTATGCGG-3' (SEQ ID NO:5); R, 5'-TCGCTATGAATATCTACTGAC-3' (SEQ ID NO:6).

aidB: F, 5'-GTCAGAGCAGATCCAGAATG-3' (SEQ ID NO:7); R, 5'-TCTACAGCAAATGAACAATG-3' (SEQ ID NO:8).

Mol_R_1: F, 5'-GGTCATCAGGTGAAATAATC-3' (SEQ ID NO:9); R, 5'-CGTCCTGATAGATAAAGTGTC-3' (SEQ ID NO:10).

fts Z: F, 5'-CAATGGAACTTACCAATGAC-3' (SEQ ID NO:11); R, 5'-TACCGCGAAGAATTCAACAC-3' (SEQ ID NO:12).

G1787979: F, 5'-AGCATCAGCGCACAATGCAC-3' (SEQ ID NO:13); R, 5'-TGTATGCAGGCTGGCACAAC-3' (SEQ ID NO:14).

yia B: F, 5'-ATAACGATCTCCATATCTAC-3' (SEQ ID NO:15) R, 5'-CTCTATCAGCAACTTCTGCC-3' (SEQ ID NO:16).

his C: F, 5'-ATCCGCAGGATTTTCGCACC-3' (SEQ ID NO:17) R, 5'-TGCCAGCGTAAATCCGCAAC-3' (SEQ ID NO:18).

*E. coli* Strains:

Non-pathogenic and pathogenic strains (and substrains) of *E. coli* screened for variation at SSR loci included K12 (DH5α, W4100, W3110), B (SR9b, SR9c), E (1, 7, 11, 18, 47, 52, 54, 63, 68, 69; see Ochman and Selander 1987), EHEC O157:H7 (FEB, Rowe no. E304810, HER 1057, 1058, 1261, 1265, 1266), EPEC (serotype O111 [Rowe no. E639616]), ETEC (serotype O78:H [Rowe no. E10407]). The K and B strains were obtained from the microbiology laboratory collection of the Department of Food Engineering and Biotechnology Technion—Israel Institute of Technology, Haifa 32000, Israel. The E strains were isolated by and obtained from Ochman and Selander (1984). The EHEC O157:H7 HER strains were isolated by and obtained from Ahmed (1987).

Preparation of *E. coli* Template DNA for PCR Amplification:

Cultures for DNA extraction were grown on LB agar plates for 24 hours at 37° C. A large loop of colonies from the plate was transferred to a microcentrifuge tube containing 500 µl of TE buffer (pH 7.5), and vortexed thoroughly. Bacterial cells were lysed at 80° C. for 10 minutes, and centrifuged for 10 minutes at 14,000 rpm (20,800×g). The pellet was suspended in 100 µl TE, boiled for 5 minutes, and centrifuged at 14,000 rpm for 2 minutes. The supernatant was held at −20° C. until used for PCR.

PCR Conditions:

Five µl of DNA extract (about 50 ng), 2.5 µl 10×PCR buffer (Promega, 25 mM $Mg^{++}$ added), 0.2 µl of 25 mM dNTPs, 1.0 units Taq polymerase (Promega), and 10 picomoles each of forward and reverse primers were brought to a final volume of 25 µl with sterile double distilled $H_2O$. Mineral oil (15–20 µl) was added for PCR in a MJ Research thermocycler without a heating cover. The cycling conditions for PCR consisted of: denaturation at 95° C. for 5 minutes, followed by 5 cycles (1 minute at 95 ° C., 1 minute at $T_m$ and 1 minutes at 72° C.), 20 cycles (1 minute at 95° C., 1 minute at $T_{m\ b-5}$° C., and 1 minute at 72° C.), a final step of 7 minutes at 72° C., and cooling to room temperature. $T_m$ stands for melting temperature and was calculated using the Generunner 3 or Oligo 4.1 software.

The following $T_m$s were employed: For the ycgW locus, 57° C.; for the yiaN locus, 62° C.; for the yjiD locus, 57° C.; for the OnaB locus, 56° C.; for the mol_R1 locus, 58° C.; for the ftsZ locus 57° C.; for the G1787979 locus, 62° C.; for the yiaB locus 58° C.; and for the hisC locus, 62° C.

End Labeling of Primers:

Radioactive end labeling of primers was as follows: 2 µl (1 ng) primer DNA, 2 µl 10×$T_4$ kinase buffer (NEB), and 4 µL $^{35}$S-γ-ATP (250 mCurie, NEN), and 1 µl (10 units) $T_4$ DNA kinase (NEB) were brought to a final volume of 20 µl with sterile double distilled $H_2O$. The contents were mixed and held at 37° C. for 1 hour. The reaction was stopped by incubation at 70° C. for 10 minutes.

Radioactive PCR:

For radioactive PCR, 0.5 µl of non-radioactive and 0.5 µl of radioactive primer (together, 10 picomoles) were used under the PCR protocol as described above.

Electrophoresis of PCR Products:

To observe small size differences among PCR products, electrophoresis of radioactive products was carried out in a 5% denaturing TBE acrylamide gel. The gels were dried (80° C. for 1.5 hours), exposed to a phosphoimager cassette, and the results were read using a Bas reader 100 (Fuji).

DNA Sequencing:

The DNA of PCR products was sequenced by the dideoxy chain termination method using an ABI automated sequencing machine (Biological Services, Weizmann Institute, Rehovot, Israel).

Experimental Results

SSRs in *E. coli*:

A computerized scan of the genome of *E. coli* revealed many small arrays of SSRs. Of 199,766 loci with simple sequence repeats (Table 1, top panel), 191,563 exhibited mononucleotide, 6,363 dinucleotide, 2,069 trinucleotide, 48 tetranucleotide, and 2 hexanucleotide core repeat length. These SSRs were distributed rather evenly throughout the genome (FIG. 1*a*). They are mostly located in non-coding areas, with the exception of those with 3 or 6 bp core sequences, which often were located in coding areas. Since the *E. coli* genome does not contain long non-coding sequences, most SSR arrays in non-coding areas were immediately upstream or immediately downstream of a gene, often in locations where variability presumably might affect gene expression (Kashi et al. 1997, King et al. 1997, Kashi and Soller 1998).

TABLE 1

Numbers of loci exhibiting given numbers of copies of simple sequence repeats for *E. coli* and 10 other genomes.

| Number of repeats Per locus | Core repeat length in nucleotides | | | | | |
|---|---|---|---|---|---|---|
| | Mono- | Di- | Tri- | Tetra- | Penta- | Hexa- |
| | *Escherichia coli* | | | | | |
| 3 | 163,476 | 7,099 | 2,364 | 51 | — | 3 |
| 4 | 42,963 | 462 | 64 | 1 | — | — |
| 5 | 13,880 | 28 | 2 | — | — | — |
| 6 | 4,119 | 1 | — | — | — | — |
| 7 | 1003 | — | — | — | — | — |
| 8 | 215 | — | — | — | — | — |

TABLE 1-continued

Numbers of loci exhibiting given numbers of copies of simple sequence repeats for *E. coli* and 10 other genomes.

| Number of repeats Per locus | Core repeat length in nucleotides | | | | | |
|---|---|---|---|---|---|---|
| | Mono- | Di- | Tri- | Tetra- | Penta- | Hexa- |
| 9 | 19 | — | — | — | — | — |
| 10 | 1 | — | — | — | — | — |
| *Aquifex aeolicus* | | | | | | |
| 3 | 79,286 | 2,870 | 697 | 34 | 1 | 6 |
| 4 | 23,911 | 181 | 28 | — | — | — |
| 5 | 8,224 | 9 | 1 | — | — | — |
| 6 | 2,176 | — | 1 | — | — | — |
| 7 | 460 | — | — | — | — | — |
| 8 | 63 | — | — | — | — | — |
| 9 | 8 | — | — | — | — | — |
| 10 | 1 | — | — | — | — | — |
| *Mycobacterium tuberculosis* | | | | | | |
| 3 | 138,899 | 7,885 | 4,249 | 68 | 9 | 18 |
| 4 | 28,602 | 614 | 249 | 1 | — | 2 |
| 5 | 5,799 | 46 | 32 | — | — | — |
| 6 | 824 | — | 1 | — | — | — |
| 7 | 137 | — | 1 | — | — | — |
| 8 | 5 | — | — | — | — | — |
| 9 | 2 | — | — | — | — | — |
| *Treponema pallidum* | | | | | | |
| 3 | 37,019 | 4,069 | 373 | 20 | — | 3 |
| 4 | 12,833 | 517 | 4 | — | — | 2 |
| 5 | 4,564 | 49 | — | — | — | — |
| 6 | 1,444 | 8 | — | — | — | — |
| 7 | 436 | — | — | — | — | — |
| 8 | 155 | — | — | — | — | — |
| 9 | 46 | — | — | — | — | — |
| 10 | 16 | — | — | — | — | — |
| 11 | 6 | — | — | — | — | — |
| 13 | 2 | — | — | — | — | — |
| *Haemophilius influenzae* | | | | | | |
| 3 | 78,444 | 1,951 | 801 | 6 | 3 | 4 |
| 4 | 27,927 | 83 | 12 | — | 1 | 1 |
| 5 | 10,399 | 5 | — | — | — | — |
| 6 | 3,892 | — | — | 1 | — | — |
| 7 | 1,045 | — | — | — | — | — |
| 8 | 145 | — | — | — | — | — |
| 9 | 16 | — | 1 | — | — | — |
| 10 | 2 | — | — | — | — | — |
| 20 | — | — | — | 1 | — | — |
| 21 | — | — | — | 1 | — | — |
| 22 | — | — | — | 1 | — | — |
| 23 | — | — | — | 4 | — | — |
| 37 | — | — | — | 1 | — | — |
| *Mycoplasma pneumoniae* | | | | | | |
| 3 | 37,389 | 671 | 345 | 9 | 1 | 3 |
| 4 | 12,113 | 24 | 8 | — | — | — |
| 5 | 4,730 | 2 | 1 | — | — | — |
| 6 | 1,455 | — | — | — | — | — |
| 7 | 360 | — | 1 | — | — | — |
| 8 | 30 | — | — | — | — | — |
| 9 | 6 | — | — | — | — | — |
| 10 | — | — | — | — | — | — |
| 11 | — | 1 | — | — | — | — |
| 15 | 1 | — | — | — | — | — |
| 16 | 2 | — | — | — | — | — |
| *Bacillus subtilis* | | | | | | |
| 3 | 16,336 | 6,530 | 1,664 | 62 | 4 | 2 |
| 4 | 56,141 | 359 | 45 | — | — | — |

TABLE 1-continued

Numbers of loci exhibiting given numbers of copies of simple sequence repeats for *E. coli* and 10 other genomes.

| Number of repeats Per locus | Core repeat length in nucleotides | | | | | |
|---|---|---|---|---|---|---|
| | Mono- | Di- | Tri- | Tetra- | Penta- | Hexa- |
| 5 | 21,322 | 16 | — | — | — | — |
| 6 | 8,009 | — | — | — | — | — |
| 7 | 2,838 | — | — | — | — | — |
| 8 | 405 | — | — | — | — | — |
| 9 | 28 | — | — | — | — | — |
| 10 | 2 | — | — | — | — | — |
| 16 | 1 | — | — | — | — | — |
| *Helicobacter pylori* | | | | | | |
| 3 | 80,371 | 2,334 | 645 | 32 | 2 | 2 |
| 4 | 35,391 | 119 | 29 | 1 | — | — |
| 5 | 15,316 | 8 | 1 | — | — | — |
| 6 | 6,462 | 2 | — | — | — | 1 |
| 7 | 1,872 | — | — | — | — | — |
| 8 | 361 | 1 | 1 | — | — | — |
| 9 | 56 | 3 | — | — | — | — |
| 10 | 6 | — | — | — | — | — |
| 11 | 2 | 3 | — | — | — | — |
| 12 | 5 | — | — | — | — | — |
| 13 | 6 | — | — | — | — | — |
| 14 | 10 | — | — | — | — | — |
| 15 | 7 | — | — | — | — | — |
| 16 | 3 | — | — | — | — | — |
| *Methanococcus jannaschii* | | | | | | |
| 3 | 77,903 | 5,368 | 1,311 | 47 | 12 | 4 |
| 4 | 28,414 | 522 | 21 | 1 | — | — |
| 5 | 11,663 | 32 | 1 | — | — | — |
| 6 | 5,069 | — | — | — | — | — |
| 7 | 1,469 | — | — | — | — | — |
| 8 | 96 | — | — | — | — | — |
| 9 | 8 | — | — | — | — | — |
| 10 | 1 | — | — | — | — | — |
| 24 | 1 | — | — | — | — | — |
| *Archaeoglobus fulgidus* | | | | | | |
| 3 | 83,655 | 4,544 | 1,107 | 24 | 4 | 2 |
| 4 | 25,167 | 392 | 21 | — | — | — |
| 5 | 8,444 | 10 | — | — | — | — |
| 6 | 2,247 | — | — | — | — | — |
| 7 | 338 | — | — | — | — | — |
| 8 | 25 | — | — | — | — | — |
| 9 | 3 | — | — | — | — | — |
| 10 | — | — | — | — | — | — |
| 15 | 1 | — | — | — | — | — |
| *Synechocystis* sp. PCC6803 | | | | | | |
| 3 | 170,790 | 2,241 | 1,516 | 41 | 6 | 4 |
| 4 | 58,969 | 88 | 83 | 1 | — | — |
| 5 | 21,668 | 9 | 14 | — | — | — |
| 6 | 6,779 | — | — | — | — | — |
| 7 | 1,596 | — | — | — | — | — |
| 8 | 325 | — | — | — | — | — |
| 9 | 56 | — | — | — | — | — |
| 10 | 15 | — | — | — | — | — |
| 11 | 1 | — | — | — | — | — |
| *Saccharomyces cerevesiae* (chromosome 7) | | | | | | |
| 3 | 43,848 | 2,252 | 642 | 43 | 12 | 18 |
| 4 | 14,253 | 193 | 44 | 4 | 2 | 3 |
| 5 | 4,755 | 32 | 14 | 1 | — | 1 |
| 6 | 1,494 | 13 | 10 | — | 1 | 1 |
| 7 | 642 | 9 | 3 | — | — | — |
| 8 | 236 | 4 | 3 | — | — | — |
| 9 | 119 | 3 | 1 | — | — | — |
| 10 | 69 | 5 | — | — | — | — |

TABLE 1-continued

Numbers of loci exhibiting given numbers of copies of simple sequence repeats for *E. coli* and 10 other genomes.

| Number of repeats Per locus | Core repeat length in nucleotides | | | | | |
|---|---|---|---|---|---|---|
| | Mono- | Di- | Tri- | Tetra- | Penta- | Hexa- |
| 11 | 49 | 4 | — | — | — | — |
| 12 | 24 | — | 1 | — | — | — |
| 13 | 26 | 1 | 1 | — | — | — |
| 14 | 16 | 2 | — | — | — | — |
| 15 | 8 | 2 | — | — | — | — |
| 16 | 5 | — | — | — | — | — |
| 17 | 3 | 2 | — | — | — | — |
| 18 | 3 | — | — | — | — | — |
| 19 | 2 | — | — | — | — | — |
| 20 | 3 | — | — | — | — | — |
| 21 | 1 | — | — | — | — | — |
| 22 | 1 | — | — | — | — | — |
| 23 | 3 | — | — | — | — | — |
| 24 | 2 | — | — | — | — | — |
| 25 | 1 | — | — | — | — | — |
| 26 | 1 | — | — | — | — | — |
| 27 | 1 | — | — | — | — | — |

Figure 2:
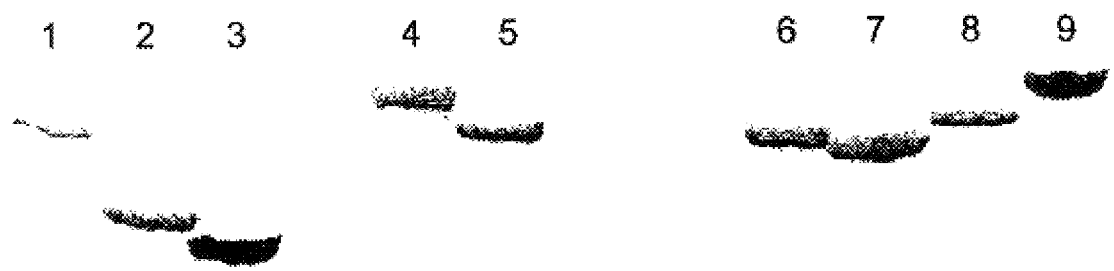
FIG. 2 demonstrates size differences in PCR products harboring specific SSR arrays among strains of *E. coli*, as shown following electrophoresis in a 5% acrylamide TBE denaturing sequencing gel. PCR was performed using primer pairs, one radiolabeled, flanking the poly-C tract at a genomic site upstream from the ATG site of the ycgW locus. The dried gel was exposed to a phosphoimager. The expected size for the K12 amplification product was about 200 bp. Shown in each lane are amplification products for the following strains: substrains (1) K12: DH5α, (2) B:SR9b, (3) B:SR9c, (4) ETEC:O78:H [E10407], (5) EPEC: O111[E639616], (6) E:1, (7) E:7, (8) E:18, (9) E:47.

Polymorphism of SSRs in *E. coli*:

The numbers of core repeats at nine SSR loci among strains or substrains of *E. coli* were determined using the polymerase chain reaction (PCR, Table 2). Differences in the sizes of PCR products were observed only in long polyacrylamide gels. At two of these loci, PCR products harboring mononucleotide SSR arrays exhibited size differences among strains of *E. coli* (FIG. 2), exhibiting several alleles. Some of the pathogenic strains did not exhibit PCR amplification, likely due to point mutations in the DNA sequence to which one or both of the primers anneal. No variation of SSR arrays was observed for core sequence lengths of two or more base pairs, although this finding may have been affected by the SSRs in question having been in coding regions and to the limited number of loci tested.

TABLE 2

Summary of allelism and location for tested SSR loci in *E. coli*.

| Strain and Substrain(s) | Number of Repeats | Core | Coding or Non-Coding Region | Genomic location, Name of ORF or Downstream ORF |
|---|---|---|---|---|
| Mononucleotide SSRs | | | | |
| K12:DH5α, K12:W3110 | 8 | C | Non-coding | G1787407, ycgW |
| BSR9b | 4 | | | |
| ETEC | 10 | | | |
| EPEC | 8 | | | |
| K12:DH5α, K12:W3110 | 10 | G | Non-coding | G1786555, yaiN |
| B SR9b | 8 | | | |
| E:1 | 10 | | | |
| E:54, E:68 | 9 | | | |
| K12, B, EHEC, EPEC, ETEC | 9 | T | Non-coding | G1790782, YjiD |
| Dinucleotide SSRs | | | | |
| K12, B, EHEC, EPEC, ETEC, E:1–69 | 4.5 | GT* | Non-coding | G1790630, aidB |
| K12, B, EHEC, EPEC, ETEC, E:1–69 | 4.5 | TC* | Non-coding | G1788433, molR_1 |

TABLE 2-continued

Summary of allelism and location for tested SSR loci in *E. coli*.

| Strain and Substrain(s) | Number of Repeats | Core | Coding or Non-Coding Region | Genomic location, Name of ORF or Downstream ORF |
|---|---|---|---|---|
| Trinucleotide SSRs | | | | |
| K12, B, EHEC, EPEC, ETEC, E:1–69 | 5 | CGG* | Coding | G1786284, fts Z |
| K12, B, EHEC, EPEC, ETEC, E:1–69 | 4 | GGT* | Non-coding | G1787973, ORF unknown |
| Tetranucleotide SSRs | | | | |
| K12, B, EHEC, EPEC, ETEC, E:1–69 | 5 | ATTA* | Non-coding | G1789986, yiaB |
| K12, B, EHEC, EPEC, ETEC, E:1–69 | 5 | CTGG* | Coding | G1788332, hisC |

*SEQ ID NOs:19–24 (in order of appearance).

Variation of mononucleotide SSRs among strains of *E. coli* was confirmed by sequencing the PCR product for the SSR and flanking domains of all nine SSR loci. Variations of DNA sequence at polymorphic loci are shown in FIG. 3. Results of DNA sequencing confirmed that the SSR arrays were hypervariable, exhibiting several alleles for copy number. Additionally, point mutations in sequences flanking the SSR arrays at both loci were the results of expansion or deletion of tandem mononucleotide repeats. The SSR polymorphisms were located just upstream of open reading frames. In addition, several point mutations involving base pair changes, but not additions or deletions, were observed among the DNA sequences of the respective strains.

Sizes of SSR Domains in Prokaryotes and Yeast:

The data presented in Table 1 show that the total lengths of particular SSR tracts in *E. coli* are small, rarely exceeding 12. Multiplying the core repeat length by the number of repeats at a given SSR locus reveals 163,476 loci of 3 bp in length, 42,963 of 4 bp, 13,880 of 5 bp, 11,218 of 6 bp, 1,003 of 7 bp, 677 of 8 bp, 2,3839 bp, 29 of 10 bp, 116 of 12 bp, 2 of 15 bp, 1 of 16 bp, 1 of 18 bp, and none of larger size. A total of 835 kb, or 18.1 percent of the *E. coli* genome, is comprised of SSR arrays (Table 3).

TABLE 3

Genomic content of simple sequence DNA repeats for 11 surveyed genomes

| Species | Genome size (Mb) | SSR content (bp) | SSR content/ genome size |
|---|---|---|---|
| *Mycoplasma pneumoniae* | 0.8 | 203,536 | 0.254 |
| *Treponema pallidum* | 1.1 | 231,714 | 0.210 |
| *Saccharomyces cerevesiae* (chromosome 7) | 1.1 | 247,720 | 0.225 |
| *Aquifex aeolicus* | 1.5 | 418,129 | 0.278 |
| *Methanococcus jannaschii* | 1.6 | 496,853 | 0.311 |
| *Helicobacter pylori* 26695 | 1.7 | 536,928 | 0.316 |
| *Haemophilius influenzae* | 1.8 | 472,757 | 0.263 |
| *Archaeoglobus fulgidus* | 2.2 | 451,024 | 0.205 |
| *Synechocystis* sp. PCC6803 | 3.6 | 941,457 | 0.262 |
| *Mycobacterium tuberculosis* | 3.7 | 661,830 | 0.178 |
| *Bacillus subtilis* | 4.2 | 510,198 | 0.121 |
| *Escherichia coli* | 4.6 | 834,618 | 0.181 |

The distribution of SSR array lengths (Table 1) and the proportion of the genome comprised of SSR arrays (Table 3)

were calculated for ten additional prokaryotes. As in *E. coli*, mononucleotide SSRs are predominant in all genomes. All prokaryote genomes examined exhibited SSRs with core sequences ranging from one to six bp, the largest core sequence for which was screened for.

In all genomes, the distribution of core repeat lengths was skewed toward mononucleotides. All genomes exhibited a distribution of total array lengths that also tended toward low numbers, three tandem repeats in most genomes. However, *Bacillus subtilis* exhibited a relatively small proportion of loci where mononucleotides where tandemly repeated three times.

The number of genomic sites exhibiting longer array lengths differed among genomes. All genomes showed 99.99% of SSR arrays at 12 or fewer bp in length. Total SSR content of the genomes varied from 12.1 to 31.6 percent, with most genomes clustered toward the middle of the range. SSRs tended to comprise a larger proportion of smaller genomes than of larger ones (Table 3).

The genomic sequence of chromosome 7 of yeast, *Saccharomyces cerevesiae*, whose length of DNA approximates that of a prokaryotic genome, was analyzed to compare the SSR content of prokaryotes with that of this simple eukaryote. *S. cerevisiae* exhibited mononucleotide arrays of greater length than observed in prokaryotes (Table 1), and a larger proportion of arrays with core repeat length greater then one. These findings for number of SSRs of given size agree perfectly with those of Field and Wills (1998). Yeast has several hundred SSR arrays larger than 12 bp. Although 99.7 of SSR arrays were of 12 or fewer bp in length in yeast, this proportion was lower than those observed in prokaryotes.

DNA Chip Design

Figure 4:
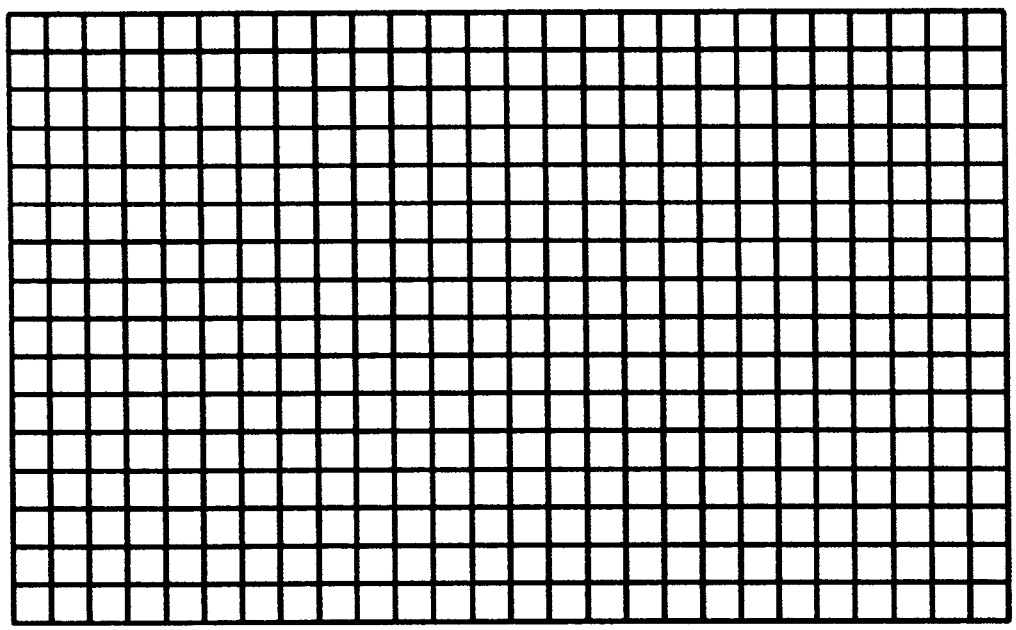
FIG. 4 is a schematic depiction of a DNA chip 10 according to the present invention, including an array of locations, each of which includes an allele specific oligonucleotide attached thereto.

FIG. 3*b* will now be employed to provide a diagrammatic example of how allele specific oligonucleotides for SSR sequences fixed onto a DNA chip, as shown at 10 in FIG. 4, can be used for strain identification in *E. coli*.

FIG. 3*b* shows a comparison of DNA sequences for five *E. coli* strains as indicated. Allelic variations at two key sites are shown in bold letters.

Allele-specific olignoucleotides are designed to distinguish among *E. coli* strains, such that $T_m$ values for all oligonucleotides are substantially equal.

Table 4 below summarized the polymorphism evident from FIG. 4.

TABLE 4

| Allele | Strains exhibiting the allele |
|---|---|
| G × 8* | Bsr9c |
| G × 9* | wt 54, wt 68 |
| G × 10* | K12:DH5α, wt 1 |
| TAAA* | wt 54, wt 68 |
| TTAA* | K12:DH5α, Bsr9c |
| TTAAA* | wt 1 |

*SEQ ID NOs: 37–42

Thus, allele-specific oligonucleotides including the specified and possibly flanking sequences will be arrayed on the surface of a DNA chip as follows:

[G×8] [G×9] [G×10] [...]

[TAAA] [TTAA] [TAAA] [...]

Genomic DNA or amplified DNA from an *E. coli* sample to be typed will be hybridized onto the chip, and the presence or absence of hybridization to each allele-specific oligonucleotide will be scored. Patterns of presence or absence of hybridization will be strain-specific. For example:

[−] [−] [+] [...]

[−] [+] [−] [...]

is diagnostic for *E. coli* strain DH5α, and

[−] [+] [−] [...]

[+] [−] [−] [...]

is diagnostic for *E. coli* strain wt 54.

LITERATURE CITED IN ALPHABETICAL ORDER (SEE ADDITIONAL LITERATURE INCORPORATED IN THE SPECIFICATION):

1. Ahmed, R. Journal of Infectious Diseases 155, 806–809 (1987).
2. Blattner, F. M., et al. The complete genome sequence of *Escherichia coli* K-12. Science 277, 1453–1462 (1997).
3. Bopp, C. A., K. D. Greene, F. P. Downes, E. Sowers, G. Wells, and I. K. Wachsmuth. Unusual verotoxin-producing *Escherichia coli* associated with hemorraghic colitis. Journal of Clinical Micorbiology 25, 1486–1489 (1987).
4. Bretagne, S., J. M. Costa, C. Besmond, R. Carsique, and R. Calderone. Microsatellite polymorphism in the promoter sequence of the elongation factor 3 gene of Candida albicans as a basis for a typing system. Journal of Clinical Microbiology 35, 1777–1780 (1997).
5. Bult, C. J., et al. Complete genome sequence of the methanogenic archaeon, Mathanococus jannaschii. Science 273, 1058–1973 (1996).
6. Chehab, F. F., J. Wall, and S. P. Cai. Analysis of PCR products by covalent reverse dot blot hybridization. Pages 130–139 in M. A. Innis, D. H. Gelfand, and J. J. Sninsky, eds. PCR strategies. Academic Press, New York (1995).
7. Chiurazzi, P., L. Kozak, and G. Neri. Unstable triplets and their mutational mechanism: size reduction of the CGG repeat versus germline mosaicism in the fragile X syndrome. American Journal of Medical Genetics 51, 517–521 (1994).
8. Claros, M. C., S. H. Gerardo, D. M. Citron, E. J. Goldstein, G. Schonian, and A. C. Rodloff. Use of the polymerase chain reaction fingerprinting to compare clinical isolates of Bacteroides fragilis and Bacteroides thetaiotaomicron from Germany and the United States. Clinical Infectious Disease 25(Suppl. 2), S295–298 (1997).
9. Coggins, L. W., and M. O'Prey. DNA tertiary structures formed in vitro by misaligned hybridization of multiple tandem repeat sequences. Nucleic Acids Research 17, 7417–7426 (1989).
10. Deckert, G., et al. The complete genome of the hyperthermophilic bacterium Aquifex aeolicus. Nature 392, 353–358 (1998).
11. Farner, J. J., and B. R. Davis. H7 antiserum-sorbitol fermentation medium for detecting *Escherichia coli* O157:H7 associated with hemorraghic colitis. Journal of Clinical Microbiology 22, 620–625 (1985).
12. Field, D., and C. Wills. Long, polymorphic microsatellites in simple organisms. Proceedings of the Royal Academy of London B 263, 209–251 (1996).

13. Field, D., and C. Wills. Abundant microsatellite polymorphism in Saccharomyces cerevisiae, and the different distributions of microsatellites in eight prokaryotes and S cerevisiae, result from strong mutation pressures and a variety of selective forces. Proc. Natl. Acad. Sci. U.S.A. 95, 1647–1652 (1998).
14. Fleischmann, R. D., et al. Whole-genome random sequencing and assembly of Haemophilus influenzae Rd. Science 269, 496–512 (1995).
15. Fraser, C. M., et al. Complete genome sequence of Treponema pallidum, the syphilis spirochete. Science 281, 375–388 (1998).
16. Hauge, X. Y., and M. Litt. A study of the origin of "shadow bands" seen when typing dinucleotide repeat polymorphisms by the PCR. Nucleic Acids Research 2, 411–415 (1993).
17. Henaut, A., F. Lisacek, P. Nitschke, I. Moszer, and A. Danchin. Global analysis of genomic texts: the distribution of ACGT tetranucleotides in the *Escherichia coli* and *Bacillus subtilis* genomes predict translational frameshifting and ribosomal hopping in several genes. Electrophoresis 19, 515–527 (1998).
18. Himmelreich, R., H. Hilbert, H. Plagens, E. Pirkl, B. Li, and R. Herrmann. Complete sequence analysis of the genome o the bacterium Mycoplasma pneumoniae. Nucleic Acids Research 24, 4421–4449 (1996).
19. Jackson, M. P. Detection of Shiga toxin-producing Shigella dysenteriae type 1 and *Escherichia coli* using the polymerase chain reaction with incorporation of digoxigenin-11-dUTP. Journal of Clinical Microbiology 29, 1910–1914 (1991).
20. Johnson, W. M., D. R. Pollard, H Lior, S. D. Tyler, and K. R. Roxee. Differentiation of genes coding for *Escherichia coli* verotoxin type 2 and the verotoxin associated with porcine edema disease (VTe) by the polymerase chain reaction. Journal of Clinical Microbiology 28, 2351–2353 (1990).
21. Johnson, W. M., S. D. Tyler, G. Wang, and H Lior. Amplification by the polymerase chain reaction of a specific target sequence in the coding for *Escherichia coli* verotoxin (Vte) variant. FEMS Microbiology Letters 84, 227–230 (1991).
22. Kaneko, T., and S. Tabata. Complete genome structure of the unicellular cyanobacterium Synechocystis sp. PCC6803. Plant and Cell Physiology 38,1171–1176 (1997).
23. Karch, H., and T. Meyers. Single primer pair for amplifying segments of distinct Shiga-like toxin genes by polymerase chain reaction. Journal of Clinical Microbiology 27, 2751–2757 (1989).
24. Karlin, S, J. Mrazek, and A. M. Campbell. Frequent oligonucleotides and peptides of the Hemophilus influenzae genome. Nucleic Acids Research 21, 4263–4272 (1996).
25. Karlin, S., J. Mrazek, and A. M. Campbell. Compositional biases of bacterial genomes and evolutionary implications. Journal of Bacteriology 179, 3899–3913 (1997).
26. Karmali, M. A. Infection by verocytotoxin-producing *Escherichia coli*. Clinical Microbiology Review 2, 15–38 (1989).
27. Kashi, Y., and M. Soller. Functional roles of microsatellites and minisatellites. In D. D. Goldstein and C. Schlotterer, eds. Microsatellite evolution and application. Oxford University Press. (1998).
28. Kashi, Y., D. King, and M. Soller. Simple sequence repeats as a source of quantitative genetic variation. Trends Genet. 13, 74–78 (1997).
29. King, D. G., M. Soller, and Y. Kashi. Evolutionary tuning knobs. Endeavor 21, 36–40 (1997).
30. Kleanthous, N., R. Fry, H. R. Smith, R. J. Gross, and B. Rowe. The use of sorbitol-McConkey in conjunction with specific antiserum for the detection of Vero cytotoxin-producing strains of *Escherichia coli* O157. Epidemiology and Infection 101, 327–335 (1988).
31. Klenk, H. P., et al. The complete genome sequence of the hyperthermophilic sulphate-reducing archaeon Archaeoglobus fulgidus. Nature 390, 364–370 (1997).
32. Kunst, F., et al. The complete genomic sequence of the gram-positive bacterium *Bacillus subtilis*. Nature 390, 249–256 (1997).
33. Kunzler, P., K. Matsuo, and W. Schaffner. Pathological, physiological, and evolutionary aspects of short unstable DNA repeats in the human genome. Biological Chemistry 376, 201–211 (1995).
34. March, S. B., and S. Ratnam. Sorbitol-McConkey medium for detection of *Escherichia coli* associated with hemorrhagic colitis. Journal of Clinical Microbiology 23, 869–972 (1986).
35. Marshall, D. G., D. C. Coleman, D. J. Sullivan, H. Xia, C. A. Morain, and C. J. Smyth. Genomic DNA fingerprinting of clinical isolates of Helicobacter pylori using short oligonucleotide probes containing repetitive sequences. Journal of Applied Bacteriology 81, 509–517 (1996).
36. Morel, P., C. Reverdy, B. Michel, S. D. Ehrlich, and E. Cassuto. The role of SOS and flap processing in microsatellite instability in *Escherichia coli*. Proceedings of the National Academy of Sciences U.S.A. 95, 10003–10008 (1998).
37. Moxon, E. R., P. R. Rainey, M. A. Nowak, and R. E. Lenski. Adaptive evolution of highly mutable loci in pathogenic bacteria. Current Biology 4, 24–33 (1994).
38. Noble, P. A., R. W. Citek, and O. A. Ogunseitan. Tetranucleotide frequencies in microbial genomes. Electrophoresis 19, 528–535 (1998).
39. Ochman, H., and R. K. Selander. Standard reference strains of *Escherichia coli* from natural populations. Journal of Bacteriology 157, 690–693 (1984).
40. Padbye, N. V., and M. P. Doyle. Production and characterization of a monoclonal antibody specific for enterohemorrhagic *Escherichia coli* O57:H7 and O26:H11. Journal of Clinical Microbiology 29, 99–103 (1991).
41. Peak, I. R. A., M. P. Jennings, D. W. Hood, M. Bisercic, and E. R. Moxon. Terameric repeat units associated with virulence factor phase variation in Hemophilus also occur in Neiserria spp. and Moraxella catarrhalis. FEMS Micorbiology Letters, 137, 109–114 (1996).
42. Pollard, D. R., W. M. Johnson, H. Lior, S. D. Tyler, and K. R. Rozee. Differentiation of Shiga toxin and verocytotoxin type 1 genes by the polymerase chain reaction. Journal of Infectious Disease. 162, 1195–1198 (1991).
43. Rosenberg, S. M., S. Longerich, P. Gee, and R. S. Harris. Adaptive mutation by deletions in small mononucleotide repeats. Science 265, 405 (1994).
44. Sambrook, J., E. F. Fristch, and T. Maniatis. Molecular cloning: A laboratory manual, second edition. Cold Spring Harbor Press, Cold Spring Harbor, N.Y. (1989).
45. Smith, H. R., and S. M. Scotland. Vero cytotoxin-producing *Escherichia coli*. Journal of Medical Microbiology 26, 77–85 (1988).
46. Strand, M., T. Prolla, R. Liskay, and T. Petes. Destabilization of tracts of simple repetitive DNA in yeast by mutations affecting DNA mismatch repair. Nature 365, 274–276 (1993).

47. Tautz, D. Hypervariability of simple sequences as a general source for polymorphic DNA markers. Nucleic Acids Research 17, 6463–6471 (1989).
48. Tautz, D., and C. Schlotterer. Title. Current Opinion in Genetics and Development 4, 832–837 (1994).
49. Tettelin, H., et al. The nucleotide sequence of Saccharomyces cerevisiae chromosome VII. Nature 387, (6632 Suppl.), 81–84 (1997).
50. Thompson, J. S., D. S. Hodge, and A. A. Borczyk. (1990). Rapid biochemical test to identify verocytotoxin-positive strains of Escherichia coli serotype O157:H7. Journal of Clinical Microbiology 28, 2165–2168.
51. Todd, E. C., R. A. Szabo, P. Peterkin, A. N. Sharpe, L. Parrington, D. Bundle, M. A. J. Gidney, and M. B. Perry. (1988). Rapid hydophobic grid membrane filter-enzyme-labeled antibody procedure for identification and enumeration of Escherichia coli O157:H7 in foods. Applied and Environmental Microbiology 54, 2536–2540.
52. Tomb, J. F. et al. The complete genome sequence of the gastric pathogen Helicobacter pylori. Nature 388, 539–547 (1997).
53. Tripathi, J., and S. K. Brahamachari. Synthesis of hybrid bacterial plasmids containing highly repeated satellite DNA. Cell 10, 509–518 (1977).
54. Tyler, S. D., W. M. Johnson, H. Lior, G. Wang, and K. R. Rozee. Identification of verotoxin type 2 variant B subunit genes in Escherichia coli by the polymerase chain reaction and restriction length polymorphism analysis. Journal of Clinical Microbiology 29, 1339–1343 (1991).
55. van Belkum, A., W. J. G. Melchers, C Ijsseldijk, L. Nohlmans, H. A. Verbrugh, and and J. F. G. M. Meis. Outbreak of amoxycillin-resistant Haemophilus influenzae type b: variable number of tandem repeats as novel molecular markers. Journal of Clinical Microbiology 35, 1517–1520 (1997a).
56. van Belkum, A., S. Scherer, L. van Alphen, and H. Verbrugh. Short-sequence DNA repeats in prokaryotic genomes. Microbiology and Molecular Biology Reviews 62, 275–293 (1998).
57. van Belkum, A., S. Scherer, W. van Leeuwen, D. Willemse, L. van Alphen, and H. A. Verbrugh. Variable number of tandem repeats in clinical strains of Haemophilus influenzae. Infectious Immunology 65, 5017–5027 (1997b).
58. Vanderzant, C., and D. F. Spittstoesser. Compendium of methods for microbiological examination of foods, third edition. Edward Brothers, Ann Arbor, Mich. (1992).
59. van Soolingen, D., P. E. W. de Haas, P. W. M. Hermans, P. M. A. Groenen, and J. D. A. van Embden. Comparison of various repetitive DNA elements as genetic markers for strain differentiation and epidemiology of Mycobacterium tuberculosis. Journal of Clinical Microbiology 31, 1987–1995 (1993).
60. Vogt, P. Potential genetic finctions of tandemly repeated DNA sequence blocks in the human genome are based on a highly conserved "chromatin folding code". Human Genetics 84, 301–336 (1990).
61. Weber, J. L. Informativeness of human poly(GT)n polymorphisms. Genomics 7, 524–530 (1990).
62. Witham, P. K., C. T. Yamashiro, K. J. Litvak, and C. A. Batt. 1996. A PCR-based assay for the detection of Escherichia coli shiga-like toxin genes in ground beef. Applied and Environmental Microbiology 62, 1347–1353.
63. Yu, J., and J. B. Kaper. Cloning and characterization of the eae gene of enterohemorhagic Escherichia coli O157:H7. Molecular Microbiology 6, 411–4417 (1992).

What is claimed is:

1. A method of classifying or typing a prokaryote to a class or a type, the method comprising the step of characterizing a plurality of polymorphic mono or dinucleotide simple sequence repeat loci, each including at least four nucleotides in at least one of its polymorphs, in a genome of said prokaryote, morph combinations of said plurality of polymorphic mono or dinucleotide simple sequence repeat loci being class or type characteristic, and, based on a characterization of said plurality of polymorphic simple sequence repeat loci, classifying or typing said prokaryote to a class or a type.

2. The method of claim 1, wherein said plurality of polymorphic simple sequence repeat loci are in non-coding regions of said genome.

3. The method of claim 1, wherein said prokaryote is of the genus Escherichia.

4. The method of claim 3, wherein said prokaryote is *Escherichia coli*.

5. The method of claim 1, wherein said prokaryote is of a genus selected from the group consisting of Aquifex, Treponema, Bacillus, Listeria and Mycobacterium.

6. The method of claim 5, wherein said prokaryote is selected from the group consisting of *Aquifex aeolicus, Treponema pallidum, Bacillus subtilis, Listeria monocytogenes* and *Mycobacterium tuberculosis*.

7. The method of claim 1, wherein said prokaryote is of a genus selected from the group consisting of Haemophilius, Mycoplasma, Helicobacter, Methanococcus, Archaeoglobus and Synechocystis.

8. The method of claim 7, wherein said prokaryote is selected from the group consisting of *Haemophilius influenzae, Mycoplasma pneumoniae, Helicobacter pylori, Methanococcus jannaschii, Archaeoglobus fulgidus* and *Synechocystis* sp. PCC6803.

9. The method of claim 1, wherein characterizing said plurality of polymorphic simple sequence repeat loci in said genome of said prokaryote is effected by allele specific oligonucleotide hybridizations.

10. The method of claim 9, wherein said allele specific oligonucleotide hybridizations is effected over a surface of DNA chip.

11. The method of claim 1, wherein characterizing said plurality of polymorphic simple sequence repeat loci in said genome of said prokaryote is effected by polymerase chain reactions.

12. The method of claim 1, wherein characterizing said plurality of polymorphic simple sequence repeat loci in said genome of said prokaryote is effected by sequencing reactions.

13. The method of claim 1, wherein characterizing said plurality of polymorphic simple sequence repeat loci in said genome of said prokaryote is effected by heteroduplex hybridization reactions.

14. The method of claim 1, wherein characterizing said plurality of polymorphic simple sequence repeat loci in said genome of said prokaryote is effected by single strand conformational polymorphisms.

15. The method of claim 1, wherein characterizing said plurality of polymorphic simple sequence repeat loci in said genome of said prokaryote is effected by restriction fragment length polymorphisms.

16. A method of classifying or typing a prokaryote of the genus Escherichia, the method comprising the step of characterizing a plurality of polymorphic simple sequence repeat loci in a genome of said prokaryote of the genus Escherichia, morph combinations of said plurality of polymorphic mono or dinucleotide simple sequence repeat loci being class or type characteristic, and, based on a characterization of said plurality of polymorphic simple sequence repeat loci, classifying or typing said prokaryote of the genus Escherichia to a class or a type.

17. A method of classifying or typing a prokaryote of interest, the method comprising the steps of:

(a) reacting a plurality of allele specific oligonucleotide probes with a genome of said prokaryote of interest, said plurality of allele specific oligonucleotide probes being complementary to a plurality of polymorphic simple sequence repeat loci of a genome of a preclassified or pretyped prokaryote, morph combinations of said plurality of polymorphic mono or dinucleotide simple sequence repeat loci being class or type characteristic;

(b) detecting a presence or an absence of hybridizations between said plurality of allele specific oligonucleotide probes and said genome of said prokaryote; and (c) according to results of said hybridizations, classifying or typing said prokaryote of interest as belonging to said preclassified or pretyped prokaryote.

* * * * *

SEQUENCE LISTING (1) GENERAL INFORMATION:

(iii) NUMBER OF SEQUENCES:42

(2) INFORMATION FOR SEQ ID NO:1:

(i) SEQUENCE CHARACTERISTICS:
      (A) LENGTH:23
      (B) TYPE:nucleic acid
      (C) STRANDEDNESS:single
      (D) TOPOLOGY:linear (xi) SEQUENCE DESCRIPTION: SEQ ID NO:1:

GATTTTGCAT ATGAGTATAT TAC      23

(2) INFORMATION FOR SEQ ID NO:2:

(i) SEQUENCE CHARACTERISTICS:
      (A) LENGTH:21
      (B) TYPE:nucleic acid
      (C) STRANDEDNESS:single
      (D) TOPOLOGY:linear (xi) SEQUENCE DESCRIPTION: SEQ ID NO:2:

TTAATTACAG GATGTTCAGT C      21

(2) INFORMATION FOR SEQ ID NO:3:

(i) SEQUENCE CHARACTERISTICS:

(A) LENGTH:21
            (B) TYPE:nucleic acid
            (C) STRANDEDNESS:single
            (D) TOPOLOGY:linear (xi) SEQUENCE DESCRIPTION: SEQ ID NO:3:

AATTTATCCG GTGAATGTGG T                                              21

(2) INFORMATION FOR SEQ ID NO:4:

(i) SEQUENCE CHARACTERISTICS:
            (A) LENGTH:20
            (B) TYPE:nucleic acid
            (C) STRANDEDNESS:single
            (D) TOPOLOGY:linear (xi) SEQUENCE DESCRIPTION: SEQ ID NO:4:

CAACTTAATC TCGGGCTGAC                                                20

(2) INFORMATION FOR SEQ ID NO:5:

(i) SEQUENCE CHARACTERISTICS:
            (A) LENGTH:19
            (B) TYPE:nucleic acid
            (C) STRANDEDNESS:single
            (D) TOPOLOGY:linear (xi) SEQUENCE DESCRIPTION: SEQ ID NO:5:

TACATGGCTG ATTATGCGG                                                 19

(2) INFORMATION FOR SEQ ID NO:6:

(i) SEQUENCE CHARACTERISTICS:
            (A) LENGTH:21
            (B) TYPE:nucleic acid
            (C) STRANDEDNESS:single
            (D) TOPOLOGY:linear (xi) SEQUENCE DESCRIPTION: SEQ ID NO:6:

TCGCTATGAA TATCTACTGA C                                              21

(2) INFORMATION FOR SEQ ID NO:7:

(i) SEQUENCE CHARACTERISTICS:
            (A) LENGTH:20
            (B) TYPE:nucleic acid
            (C) STRANDEDNESS:single
            (D) TOPOLOGY:linear (xi) SEQUENCE DESCRIPTION: SEQ ID NO:7:

GTCAGAGCAG ATCCAGAATG                                                20

(2) INFORMATION FOR SEQ ID NO:8:

(i) SEQUENCE CHARACTERISTICS:
            (A) LENGTH:20
            (B) TYPE:nucleic acid
            (C) STRANDEDNESS:single
            (D) TOPOLOGY:linear (xi) SEQUENCE DESCRIPTION: SEQ ID NO:8:

TCTACAGCAA ATGAACAATG                                                20

(2) INFORMATION FOR SEQ ID NO:9:

(i) SEQUENCE CHARACTERISTICS:
            (A) LENGTH:20

(B) TYPE:nucleic acid
        (C) STRANDEDNESS:single
        (D) TOPOLOGY:linear (xi) SEQUENCE DESCRIPTION: SEQ ID NO:9:

GGTCATCAGG TGAAATAATC                                              20

(2) INFORMATION FOR SEQ ID NO:10:

(i) SEQUENCE CHARACTERISTICS:
        (A) LENGTH:21
        (B) TYPE:nucleic acid
        (C) STRANDEDNESS:single
        (D) TOPOLOGY:linear (xi) SEQUENCE DESCRIPTION: SEQ ID NO:10:

CGTCCTGATA GATAAAGTGT C                                            21

(2) INFORMATION FOR SEQ ID NO:11:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:11:

CAATGGAACT TACCAATGAC                                              20

(2) INFORMATION FOR SEQ ID NO:12:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:12:

TACCGCGAAG AATTCAACAC                                              20

(2) INFORMATION FOR SEQ ID NO:13:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:13:

AGCATCAGCG CACAATGCAC                                              20

(2) INFORMATION FOR SEQ ID NO:14:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:14:

TGTATGCAGG CTGGCACAAC                                              20

(2) INFORMATION FOR SEQ ID NO:15:

(i) SEQUENCE CHARACTERISTICS:
        (A) LENGTH:20
        (B) TYPE:nucleic acid

```
        (C) STRANDEDNESS:single
        (D) TOPOLOGY:linear (xi) SEQUENCE DESCRIPTION: SEQ ID NO:15:

ATAACGATCT CCATATCTAC                                               20

(2) INFORMATION FOR SEQ ID NO:16:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:16:

CTCTATCAGC AACTTCTGCC                                               20

(2) INFORMATION FOR SEQ ID NO:17:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:17:

ATCCGCAGGA TTTTCGCACC                                               20

(2) INFORMATION FOR SEQ ID NO:18:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION: SEQ ID NO:18:

TGCCAGCGTA AATCCGCAAC                                               20

(2) INFORMATION FOR SEQ ID NO:19:

(i) SEQUENCE CHARACTERISTICS:
        (A) LENGTH:2
        (B) TYPE:nucleic acid
        (C) STRANDEDNESS:double
        (D) TOPOLOGY:linear (xi) SEQUENCE DESCRIPTION: SEQ ID NO:19:

GT                                                                   2

(2) INFORMATION FOR SEQ ID NO:20:

(i) SEQUENCE CHARACTERISTICS:
        (A) LENGTH:2
        (B) TYPE:nucleic acid
        (C) STRANDEDNESS:double
        (D) TOPOLOGY:linear (xi) SEQUENCE DESCRIPTION: SEQ ID NO:20:

TC                                                                   2

(2) INFORMATION FOR SEQ ID NO:21:

(i) SEQUENCE CHARACTERISTICS:
        (A) LENGTH:3
        (B) TYPE:nucleic acid
        (C) STRANDEDNESS:double
```

(D) TOPOLOGY:linear (xi) SEQUENCE DESCRIPTION: SEQ ID NO:21:

CGG                                                                          3

(2) INFORMATION FOR SEQ ID NO:22:

(i) SEQUENCE CHARACTERISTICS:
            (A) LENGTH:3
            (B) TYPE:nucleic acid
            (C) STRANDEDNESS:double
            (D) TOPOLOGY:linear (xi) SEQUENCE DESCRIPTION: SEQ ID NO:22:

GGT                                                                          3

(2) INFORMATION FOR SEQ ID NO:23:

(i) SEQUENCE CHARACTERISTICS:
            (A) LENGTH:4
            (B) TYPE:nucleic acid
            (C) STRANDEDNESS:double
            (D) TOPOLOGY:linear (xi) SEQUENCE DESCRIPTION: SEQ ID NO:23:

ATTA                                                                         4

(2) INFORMATION FOR SEQ ID NO:24:

(i) SEQUENCE CHARACTERISTICS:
            (A) LENGTH:4
            (B) TYPE:nucleic acid
            (C) STRANDEDNESS:double
            (D) TOPOLOGY:linear (xi) SEQUENCE DESCRIPTION: SEQ ID NO:24:

CTGG                                                                         4

(2) INFORMATION FOR SEQ ID NO:25:

(i) SEQUENCE CHARACTERISTICS:
            (A) LENGTH:259
            (B) TYPE:nucleic acid
            (C) STRANDEDNESS:double
            (D) TOPOLOGY:linear (xi) SEQUENCE DESCRIPTION: SEQ ID NO:25:

GTTATGTCTT ATCCCACGGT ATTTAATATG GTTCATTAGG ATGTTTATTT                       50

CTTGATTTTG CATATGAGTA TATTACCCCC CCCTCAAAAA AATAAATTAA                      100

TTAAAATGAT GGCTTATATA AAATAAAATT TAAAGCAAGG AATCTCAATG                      150

GATGTTAAAC AAAATGAGAT TTTGTGAAAG CAATAAATTA TTGACTTCGT                      200

TTTAGATTTG TTTAGCTATA ATGTTATACA TTCAAATGAC TGAACATCCT                      250

GTAATTAAA                                                                  259

(2) INFORMATION FOR SEQ ID NO:26:

(i) SEQUENCE CHARACTERISTICS:
            (A) LENGTH:256
            (B) TYPE:nucleic acid
            (C) STRANDEDNESS:double
            (D) TOPOLOGY:linear (xi) SEQUENCE DESCRIPTION: SEQ ID NO:26:

```
TTGTTATGTC TTATCCCACG GTATTTAATA TAGTTCATTT GGATGTTCAT            50

TTCTTTATTT TGCATATGAG TATATTACCC CTTCAAAAAA TAAATTAATT           100

AAAACGATTG CTTATATAAA ACAAAATTTA AAGCAAGGAA TCTCAATGGA           150

TGTTAAACAA AATGAGATTT AGTGAAAACA ATAAATTATT CACTTCGTTT           200

TAGATTTGTT TAGCTATAAT GTTATACATT CAAATGACTG AACATCCTGT           250

ATTTAA                                                          256

(2) INFORMATION FOR SEQ ID NO:27:

(i) SEQUENCE CHARACTERISTICS:
        (A) LENGTH:257
        (B) TYPE:nucleic acid
        (C) STRANDEDNESS:double
        (D) TOPOLOGY:linear (xi) SEQUENCE DESCRIPTION: SEQ ID NO:27:

TTTGTTATGT CTTATCCCAC GGTATTTAAT ATAGTTCATT TGGATGTTCA            50

TTTCTTTATT TTGCATATGA GTATATTACC CCTTCAAAAA ATAAATTAAT           100

TAAAACGATT GCTTATATAA AACAAAATTT AAAGCAAGGA ATCTCAATGG           150

ATGTTAAACA AAATGAGATT TAGTGAAAAC AATAAATTAT TCACTTCGTT           200

TTAGATTTGT TTAGCTATAA TGTTATACAT TCAAATGACT GAACATCCTG           250

TAATTAA                                                         257

(2) INFORMATION FOR SEQ ID NO:28:

(i) SEQUENCE CHARACTERISTICS:
        (A) LENGTH:263
        (B) TYPE:nucleic acid
        (C) STRANDEDNESS:double
        (D) TOPOLOGY:linear (xi) SEQUENCE DESCRIPTION: SEQ ID NO:28:

TCTATGTTCT TATCNCCACG GTNTTTAATA TGGTTCATTA GGATGTTTAT            50

TTCTTGATTT TGCATATGAG TATATTACCC CCCCCCCTCA AAAAAATAAA           100

TTAATTAAAA TGATGGCTTA TATNAAATAN AATTTAAAGC AAGGANTCTC           150

AATGGATGTT AAACANAATG AGATTTTGTG AANGCNATNN ATTATTGNCT           200

TCGTTGTANA TTTGCTNAGC TATAATGTTA TNCATTCAAA TGACTGAACA           250

TCCTGTNNTT ANA                                                  263

(2) INFORMATION FOR SEQ ID NO:29:

(i) SEQUENCE CHARACTERISTICS:
        (A) LENGTH:264
        (B) TYPE:nucleic acid
        (C) STRANDEDNESS:double
        (D) TOPOLOGY:linear (xi) SEQUENCE DESCRIPTION: SEQ ID NO:29:

NNNNNTNTNN NTNNNCCCAC GGTATTTAAT ATNGTTCATT NGGATGTTNA            50

TTTCTTNATT TTGCATATGA GTATATTANN NNNNCCCCTN NAAAAAATAA           100

ATTAATTAAA ANGATNGCTT ATATAAAANA AAATTTAAAG CAAGGAATCT           150

CAATGGATGT TAAACAAAAT GAGATTTNGT GAAANCAATA AATTATTNAC           200

TTCGTTNTAG ATTTGNTTAG CTATAATGTT ATACATTCAA ATGACTGAAC           250
```

ATCCTGTAAT TAAN                                                  264

(2) INFORMATION FOR SEQ ID NO:30:

(i) SEQUENCE CHARACTERISTICS:
        (A) LENGTH:181
        (B) TYPE:nucleic acid
        (C) STRANDEDNESS:double
        (D) TOPOLOGY:linear (xi) SEQUENCE DESCRIPTION: SEQ ID NO:30:

TTTNCCCGGA AAAAAATAGG AAAGGGGGGG GGGCTAATCG GCAGGGAAGG            50

CCGCCCCGGA TAGCGGGCGG CANAAGGAAT CANAATTTCC AGGTCAGACG            100

GGCTGCAAGT TGCAGACCGT TAAAATCATC GGNNGGGGTG TCGTACCACA            150

CTTTACCTGC CGTCAGCCCG AGATTAAGTT G                                181

(2) INFORMATION FOR SEQ ID NO:31:

(i) SEQUENCE CHARACTERISTICS:
        (A) LENGTH:181
        (B) TYPE:nucleic acid
        (C) STRANDEDNESS:double
        (D) TOPOLOGY:linear (xi) SEQUENCE DESCRIPTION: SEQ ID NO:31:

TNTTNNNCGG AAAAAAATNG AAAGGGGGGG GGGCTAATCG GCAGGGAAGG            50

CCGCCCCGGA TAGCGGGCGG CAGAAGGAAT CAGAATTTCC AGGTCAGACG            100

GGCTGCAAGT TGCAGACCGT TAAAATCATC GGTTGGGGTG TCGTACCACA            150

CTTTACCTGC CGTCAGCCCG AGATTAAGTT G                                181

(2) INFORMATION FOR SEQ ID NO:32:

(i) SEQUENCE CHARACTERISTICS:
        (A) LENGTH:177
        (B) TYPE:nucleic acid
        (C) STRANDEDNESS:double
        (D) TOPOLOGY:linear (xi) SEQUENCE DESCRIPTION: SEQ ID NO:32:

TTTNCCGGAA AAAAATNGAA AGGGGGGGGC TAATCGGCAG GGAAGGCCGC            50

CCCGGATAGC GGGCGGCAGA AGGAATCAGA ATTTCCAGGT CAGATGGGCT            100

GCAAGTTGCA GACCGTTATA ATCATCGGTT GGGGTGTCGT ACCACACTTT            150

ACCTGCCGTC AGCCCGAGAT TAAGTTG                                    177

(2) INFORMATION FOR SEQ ID NO:33:

(i) SEQUENCE CHARACTERISTICS:
        (A) LENGTH:182
        (B) TYPE:nucleic acid
        (C) STRANDEDNESS:double
        (D) TOPOLOGY:linear (xi) SEQUENCE DESCRIPTION: SEQ ID NO:33:

TNTNCGGAAA AAAANAGGAA AGGGGGGGGG GCTAATCGGC AGGGAAGGCC            50

GCCCCGGATA GCGGGCGGCA GAAGGAATCA GAATTTCCAG GTCAGACGGG           100

CTGCAAGTTG CAGACCGTTA AAATCATCGG TTGGGGTGTC GTACCACACT           150

TTACCTGCCG TCAGCCCGAG ATTAAAGTTT GG                              182

(2) INFORMATION FOR SEQ ID NO:34:

(i) SEQUENCE CHARACTERISTICS:
        (A) LENGTH:175
        (B) TYPE:nucleic acid
        (C) STRANDEDNESS:double
        (D) TOPOLOGY:linear (xi) SEQUENCE DESCRIPTION: SEQ ID NO:34:

```
NCGGAAAAAA ATGAAAGGGG GGGGGCTAAT CGGCAGGGAA GGCCGCCCCG        50

GATAGCGGGC GGCAGAAGGA ATCAGAATTT CCAGGTCAGA TGGGCTGCAA       100

GTTGCAGACC GTTATAATCA TCGGTTGGGG TGTCGTACCA CACTTTACCT       150

GCCGTCAGCC CGAGATAAAG TTTGG                                 175
```

(2) INFORMATION FOR SEQ ID NO:35:

(i) SEQUENCE CHARACTERISTICS:
        (A) LENGTH:174
        (B) TYPE:nucleic acid
        (C) STRANDEDNESS:double
        (D) TOPOLOGY:linear (xi) SEQUENCE DESCRIPTION: SEQ ID NO:35:

```
CGGAAAAAAA TGAAAGGGGG GGGGCTAATC GGCAGGGAAG GCCGCCCCGG        50

ATAGCGGGCG GCAGAAGGAA TCAGAATTTC CAGGTCAGAT GGGCTGCAAG       100

TTGCAGACCG TTATAATCAT CGGTTGGGGT GTCGTACCAC ACTTTACCTG       150

CCGTCAGCCC GAGATAAAGT TTGG                                  174
```

(2) INFORMATION FOR SEQ ID NO:36:

(i) SEQUENCE CHARACTERISTICS:
        (A) LENGTH:182
        (B) TYPE:nucleic acid
        (C) STRANDEDNESS:double
        (D) TOPOLOGY:linear (xi) SEQUENCE DESCRIPTION: SEQ ID NO:36:

```
NNNNNNNNNN NAAAAAANNG AAANNGGGGG GGGCTAATCG GCAGGGAAGG        50

CCGCCCCGGA TAGCGGGCGG CAGAAGGAAT CAGAATTTCC AGGTCAGANG       100

GCTGCAAGT TGCAGACCGT TANAATCATC GGTTGGGGTG TCGTACCACA       150

CTTTACCTGC CGTCAGCCCG AGATNAAGTT NG                         182
```

(2) INFORMATION FOR SEQ ID NO:37:

(i) SEQUENCE CHARACTERISTICS:
        (A) LENGTH:8
        (B) TYPE:nucleic acid
        (C) STRANDEDNESS:single
        (D) TOPOLOGY:linear (xi) SEQUENCE DESCRIPTION: SEQ ID NO:37:

```
GGGGGGGG                                                      8
```

(2) INFORMATION FOR SEQ ID NO:38:

(i) SEQUENCE CHARACTERISTICS:
        (A) LENGTH:9
        (B) TYPE:nucleic acid
        (C) STRANDEDNESS:single
        (D) TOPOLOGY:linear (xi) SEQUENCE DESCRIPTION: SEQ ID NO:38:

```
GGGGGGGGG                                                                9

(2) INFORMATION FOR SEQ ID NO:39:

(i) SEQUENCE CHARACTERISTICS:
        (A) LENGTH:10
        (B) TYPE:nucleic acid
        (C) STRANDEDNESS:single
        (D) TOPOLOGY:linear (xi) SEQUENCE DESCRIPTION: SEQ ID NO:39:

GGGGGGGGGG                                                               10

(2) INFORMATION FOR SEQ ID NO:40:

(i) SEQUENCE CHARACTERISTICS:
        (A) LENGTH:4
        (B) TYPE:nucleic acid
        (C) STRANDEDNESS:single
        (D) TOPOLOGY:linear (xi) SEQUENCE DESCRIPTION: SEQ ID NO:40:

TAAA                                                                     4

(2) INFORMATION FOR SEQ ID NO:41:

(i) SEQUENCE CHARACTERISTICS:
        (A) LENGTH:4
        (B) TYPE:nucleic acid
        (C) STRANDEDNESS:single
        (D) TOPOLOGY:linear (xi) SEQUENCE DESCRIPTION: SEQ ID NO:41:

TTAA                                                                     4

(2) INFORMATION FOR SEQ ID NO:42:

(i) SEQUENCE CHARACTERISTICS:
        (A) LENGTH:5
        (B) TYPE:nucleic acid
        (C) STRANDEDNESS:single
        (D) TOPOLOGY:linear (xi) SEQUENCE DESCRIPTION: SEQ ID NO:42:

TTAAA                                                                    5
```